(12) United States Patent
Coleman et al.

(10) Patent No.: US 10,182,736 B2
(45) Date of Patent: Jan. 22, 2019

(54) CONFIGURATION AND SPATIAL PLACEMENT OF FRONTAL ELECTRODE SENSORS TO DETECT PHYSIOLOGICAL SIGNALS

(71) Applicants: The Regents of the University of California, Oakland, CA (US); The Salk Institute for Biological Studies, La Jolla, CA (US)

(72) Inventors: Todd Prentice Coleman, La Jolla, CA (US); Rui Ma, San Diego, CA (US); Michael Bajema, San Diego, CA (US); Ricardo Gil Da Costa, San Diego, CA (US); Raynard Fung, La Jolla, CA (US)

(73) Assignees: The Regents of the University of California, Oakland, CA (US); The Salk Institute for Biological Studies, La Jolla, CA (US)

( * ) Notice: Subject to any disclaimer, the term of this patent is extended or adjusted under 35 U.S.C. 154(b) by 75 days.

(21) Appl. No.: 14/435,398

(22) PCT Filed: Oct. 14, 2013

(86) PCT No.: PCT/US2013/064892
§ 371 (c)(1),
(2) Date: Apr. 13, 2015

(87) PCT Pub. No.: WO2014/059431
PCT Pub. Date: Apr. 17, 2014

(65) Prior Publication Data
US 2015/0313498 A1    Nov. 5, 2015

Related U.S. Application Data

(60) Provisional application No. 61/713,339, filed on Oct. 12, 2012.

(51) Int. Cl.
*A61B 5/0478* (2006.01)
*A61B 5/0484* (2006.01)
(Continued)

(52) U.S. Cl.
CPC ........ *A61B 5/0478* (2013.01); *A61B 5/04012* (2013.01); *A61B 5/0482* (2013.01);
(Continued)

(58) Field of Classification Search
CPC .................................................. A61B 5/0478
See application file for complete search history.

(56) References Cited

U.S. PATENT DOCUMENTS 3,896,790 A * 7/1975 Dikmen ............... A61B 5/0476
600/383
4,092,981 A   6/1978 Ertl
(Continued)

FOREIGN PATENT DOCUMENTS

CN    101296554 A    10/2008
CN    101500471 A    8/2009
(Continued)

OTHER PUBLICATIONS

International Search Report and Written Opinion of PCT/US2013/064892 mailed by the Korean Intellectual Property Office dated Apr. 11, 2014 (14 pages).
(Continued)

*Primary Examiner* — Lee S Cohen
(74) *Attorney, Agent, or Firm* — Perkins Coie LLP

(57) ABSTRACT

Methods, systems, and devices are disclosed for acquiring and analyzing physiological signals. In one aspect, a physiological sensor device includes a substrate formed of an electrically insulative material and structured to allow physical contact of the device with the frontal region of the head of a user, a recording electrode configured at a first location
(Continued)

on the substrate to acquire an electrophysiological signal of the user, a reference electrode configured at a second location on the substrate to acquire a reference signal to the electrophysiological signal, and a ground electrode configured at a third location at least partially between the first and the second locations on the substrate, in which the first location is posterior to the second and third locations, and in which the device is operable when electrically coupled to an electrical circuit to detect physiological signals of the user.

26 Claims, 22 Drawing Sheets

(51) Int. Cl.
*A61B 5/0492* (2006.01)
*A61B 5/00* (2006.01)
*A61B 5/04* (2006.01)
*A61B 5/0482* (2006.01)
A61B 5/0488 (2006.01)
A61B 5/16 (2006.01)

(52) U.S. Cl.
CPC .......... *A61B 5/0484* (2013.01); *A61B 5/0492* (2013.01); *A61B 5/04842* (2013.01); *A61B 5/04845* (2013.01); *A61B 5/04847* (2013.01); *A61B 5/6803* (2013.01); *A61B 5/0488* (2013.01); *A61B 5/165* (2013.01); *A61B 5/167* (2013.01); *A61B 5/168* (2013.01); *A61B 5/6814* (2013.01)

(56) References Cited

U.S. PATENT DOCUMENTS

| | | | |
|---|---|---|---|
| 4,595,013 A * | 6/1986 | Jones | A61B 5/04085 600/383 |
| 4,987,903 A | 1/1991 | Keppel et al. | |
| RE34,015 E | 8/1992 | Duffy | |
| 5,406,956 A | 4/1995 | Farwell | |
| 6,032,065 A | 2/2000 | Brown | |
| 6,061,593 A | 5/2000 | Fischell et al. | |
| 6,272,378 B1 * | 8/2001 | Baumgart-Schmitt | A61B 5/0476 600/544 |
| 6,463,328 B1 | 10/2002 | John | |
| 6,654,626 B2 * | 11/2003 | Devlin | A61B 5/04085 600/372 |
| 6,751,499 B2 * | 6/2004 | Lange | A61B 5/0478 600/300 |
| 6,832,110 B2 | 12/2004 | Sohmer et al. | |
| 6,947,790 B2 | 9/2005 | Gevins et al. | |
| 7,130,673 B2 * | 10/2006 | Tolvanen-Laakso | A61B 5/0478 600/383 |
| 7,338,455 B2 | 3/2008 | White et al. | |
| D597,676 S | 8/2009 | Copeland et al. | |
| 7,986,691 B2 | 7/2011 | Park et al. | |
| 7,986,991 B2 | 7/2011 | Prichep | |
| 8,221,330 B2 | 7/2012 | Sarkela et al. | |
| 8,588,883 B2 * | 11/2013 | Jadidi | A61B 5/0492 600/372 |
| 2002/0019588 A1 * | 2/2002 | Marro | A61B 5/0478 600/383 |
| 2003/0013981 A1 | 1/2003 | Gevins et al. | |
| 2003/0032870 A1 | 2/2003 | Farwell | |
| 2003/0073921 A1 | 4/2003 | Sohmer et al. | |
| 2004/0002635 A1 | 1/2004 | Hargrove et al. | |
| 2004/0204656 A1 | 10/2004 | Tolvanen-Laakso et al. | |
| 2005/0021104 A1 | 1/2005 | DiLorenzo | |
| 2005/0143629 A1 | 6/2005 | Farwell | |
| 2005/0273017 A1 | 12/2005 | Gordon | |
| 2006/0183981 A1 | 8/2006 | Skinner | |
| 2006/0293608 A1 * | 12/2006 | Rothman | A61B 5/4812 600/545 |
| 2007/0100214 A1 | 5/2007 | Steinert | |
| 2007/0106169 A1 | 5/2007 | Fadem | |
| 2007/0191727 A1 | 8/2007 | Fadem | |
| 2008/0221422 A1 | 9/2008 | Rantala | |
| 2008/0249430 A1 | 10/2008 | John et al. | |
| 2009/0105577 A1 * | 4/2009 | Wu | A61B 5/0478 600/383 |
| 2009/0214060 A1 | 8/2009 | Chuang et al. | |
| 2009/0216091 A1 | 8/2009 | Arndt | |
| 2009/0220425 A1 | 9/2009 | Moxon et al. | |
| 2009/0227889 A2 | 9/2009 | John et al. | |
| 2010/0010336 A1 | 1/2010 | Pettegrew et al. | |
| 2010/0041962 A1 | 2/2010 | Causevic et al. | |
| 2010/0099954 A1 | 4/2010 | Dickinson et al. | |
| 2010/0274152 A1 | 10/2010 | McPeck et al. | |
| 2011/0098593 A1 | 4/2011 | Low et al. | |
| 2011/0109879 A1 | 5/2011 | Palti-Wasserman et al. | |
| 2012/0041330 A1 * | 2/2012 | Prichep | A61B 5/0478 600/544 |
| 2012/0071781 A1 | 3/2012 | Fadem | |
| 2012/0094315 A1 | 4/2012 | Fryar-Williams | |
| 2012/0150545 A1 | 6/2012 | Simon | |
| 2012/0191000 A1 | 7/2012 | Adachi et al. | |
| 2012/0221075 A1 | 8/2012 | Bentwich | |
| 2012/0253163 A1 | 10/2012 | Afanasewicz et al. | |
| 2013/0079618 A1 * | 3/2013 | Sandmore | A61B 5/0478 600/393 |
| 2013/0127708 A1 * | 5/2013 | Jung | A61B 5/0006 345/156 |
| 2013/0172721 A1 * | 7/2013 | McPeck | A61B 5/0478 600/383 |

FOREIGN PATENT DOCUMENTS

| | | |
|---|---|---|
| EP | 1468646 A2 | 10/2004 |
| JP | 2001502217 A | 2/2001 |
| JP | 2008-503261 A | 2/2008 |
| JP | 2009-521246 A | 6/2009 |
| JP | 2009-542276 A | 12/2009 |
| JP | 2010-526379 A | 7/2010 |
| JP | 2011-186667 A | 9/2011 |
| KR | 1020060085543 A | 7/2006 |
| KR | 102012011030 A | 10/2012 |
| WO | 2006003901 A | 12/2006 |
| WO | WO-2009044271 A2 | 4/2009 |
| WO | WO-2011109716 A2 | 9/2011 |
| WO | WO-2011160222 A1 | 12/2011 |

OTHER PUBLICATIONS

Coleman et al., "Epidermal electronics capture of event-related brain potentials (ERP) signal in a 'real-world' target detection task", poster presentation at Society for Neuroscience Annual Meeting, Oct. 14, 2012.

Garrido et al. "The mismatch negativity: A review of underlying mechanisms," Clinical Neurophysiology, Mar. 2009, 120, 453-463.

Gil Da Costa, et al. "Support for a non-human primate model of schizophrenia: acute subanesthetic ketamine reduces mismatch negativity (MMN) and P3", poster presentation at Society for Neuroscience Annual Meeting, Nov. 13, 2011.

Heekeren et al. "Mismatch negativity generation in the human 5HT2A agonist and NMDA antagonist model of psychosis." Psychopharmacology (Berl). Jul. 2008; 199(1): 77-88.

Huang et al. "Stimulus dependency and mechanisms of surround modulation in cortical area MT," Journal of Neuroscience Dec. 17, 2008, 28 (51) 13889-13906.

Javitt, et al. "Demonstration of mismatch negativity in the monkey," Aug. 1992 Electroencephalography and Clinical Neurophysiology. 83, 87-90.

Johnstone, et al. "Predicting schizophrenia: findings from the Edinburgh High-Risk Study," The British Journal of Psychiatry, Jan. 2005, 186 (1) 18-25.

Kim, D.-H. et al., "Epidermal Electronics", *Science*, vol. 333, 2011, pp. 838-843.

(56) References Cited

OTHER PUBLICATIONS

Kim, S. et al., "Efficient Bayesian Inference Methods via Convex Optimization and Optimal Transport", Information Theory Proceedings (ISIT), 2013 IEEE International Symposium, pp. 2259-2263.
Liao, L.-D. et al., "Biosensor technologies for augmented brain-computer interfaces in the next decades," Proc. IEEE, vol. 100, 2012, pp. 1553-1566.
Lieberman, J. A. et al., "Effectiveness of antipsychotic drugs in patients with chronic schizophrenia," The New England Journal of Medicine, Sep. 2005, 353, 1209-1223.
Ma, R. et al., "Generalizing the Posterior Matching Scheme to Higher Dimensions via Optimal Transportation", Allerton Conference on Communication, Control, and Computing, Sep. 2011, 7 pages.
Makeig, S. et al., "Evolving signal processing for brain-computer interfaces," Proc. IEEE, vol. 100, 2012, pp. 1567-1584.
Näätänen, R. et al. "'Primitive intelligence' in the auditory cortex," TRENDS in Neurosciences, Jun. 2001, 24, 283-288.
Näätänen, R. et al., "The mismatch negativity (MMN)—A unique window to disturbed central auditory processing in ageing and different clinical conditions," Clinical Neurophysiology 2012, vol. 123, 424-458.
Oh, e. g., authorized Officer, Korean Intellectual Property Office, International Search Report and Written Opinion, International Patent Application No. PCT/US2013/069520, dated Feb. 24, 2014, 15 pages.
Omar, C. et al., "A Feedback Information-Theoretic Approach to the Design of Brain-Computer Interfaces", International Journal on Human-Computer Interaction, 27(1), Jan. 2011, pp. 5-23.
Rissanen, J., "Hypothesis selection and testing by the MDL principle," The Computer Journal, vol. 42, No. 4, 1999, pp. 260-269.
Sellers, E. W. et al., "A P300-based brain-computer interface: Initial tests by ALS patients", Clinical Neurophysiology 117 (2006) 538-548.
Shayevitz, O. et al., "Optimal Feedback Communication via Posterior Matching", IEEE Transactions on Information Theory, vol. 57, No. 3, Mar. 2011, pp. 1186-1222.
Sutton et al., "Evoked-potentials correlates of stimulus uncertainty," Science, Nov. 26, 1965, vol. 150, No. 3700, pp. 1187-1188.
Toomey, et al., "Why do children with ADHD discontinue their medication?" Clinical Pediatrics, 2012, 51(8) 763-769.
Umbricht, D. et al., "Ketamine-induced deficits in auditory and visual context-dependent processing in healthy volunteers: implications for models of cognitive deficits in schizophrenia," Arch Gen Psychiatry, Dec. 2000; 57(12):1139-47.
Van Der Stelt, et al. "Application of electroencephalography to the study of cognitive and brain functions in schizophrenia," Schizophrenia Bulletin, Jul. 2007; 33(4): 955-970.
Vecchio, et al. "The Use of Auditory Event-Related Potentials in Alzheimer's Disease Diagnosis," International Journal of Alzheimer's Disease vol. 2011 (2011), Article ID 653173.
Ward, D. et al., "Fast Hands-free Writing by Gaze Direction", Nature, vol. 418, Aug. 22, 2002, p. 838.
Ward, D.J. et al., "Dasher—a Data Entry Interface Using Continuous Gestures and Language Models.", In proceedings UIST 2000, 10 pages.
Wynn, et al.,"Mismatch negativity, social cognition, and functioning in schizophrenia patients," Biological Psychiatry 2010; 67, 940-947.
Zander, T.O. et al., "Towards passive brain-computer interfaces: applying brain-computer interface technology to human-machine systems in general", J. Neural Eng. 8, 2011, pp. 1-5.
Pilgreen, KL, "Physiologic, medical, and cognitive correlates of electroencephalography." In P. L. Nunez (Ed.), Neocortical dynamics and EEG rhythms, pp. 195-248. New York: Oxford University Press, 1995.
International Search Report and Written Opinion issued in PCT/US2013/062491 by the Korean Intellectual Property Office dated Jan. 17, 2014.
Extended European Search Report for European Application No. 13845002.8; dated Apr. 28, 2016.
Extended European Search Report for European Application No. 13842699.4; dated May 24, 2016.
Extended European Search Report for European Application No. 13852926.8; dated Sep. 28, 2016.
"Statistics: Any Disorder Among Adults". National Institute of Mental Health. National Institutes of Health. http://www.nimh.nih.gov/statistics/1ANYDIS_ADULT.shtml.
"What is Schizophrenia?". National Institute of Mental Health. Sep. 8, 2009. National Institutes of Health. http://www.nimh.nih.gov/health/publications/schizophrenia/what-is-schizophrenia.shtml.
Breggin, P.R., A misdiagnosis, anywhere. The New York Times. http://www.nytimes.com/roomfordebate/2011/10/12/are-americans-more-prone-to-adhd/adhd-is-a-misdiagnosis.
Partial Supplementary European Search Report for European Application No. 13852926.8; dated Jun. 6, 2016.
Chinese Office Action for Chinese Application No. 201380058415.8; dated Dec. 8, 2016.
Chinese Office Action for Chinese Application No. 201380058185.5; dated Mar. 3, 2017.
Chinese Office Action for Chinese Application No. 201380060011.2; dated Oct. 8, 2016.
Chinese Office Action for Chinese Application No. 201380060011.2; dated May 19, 2017.
Japanese Office Action for Japanese Application No. 2015-534783, dated Aug. 3, 2017.
Japanese Office Action for Japanese Application No. 2015-536992, dated Sep. 29, 2017, 3 pages.
Decision of Refusal for Japanese Patent Application No. 2015-536992, dated May 10, 2018, 2 pages.

* cited by examiner

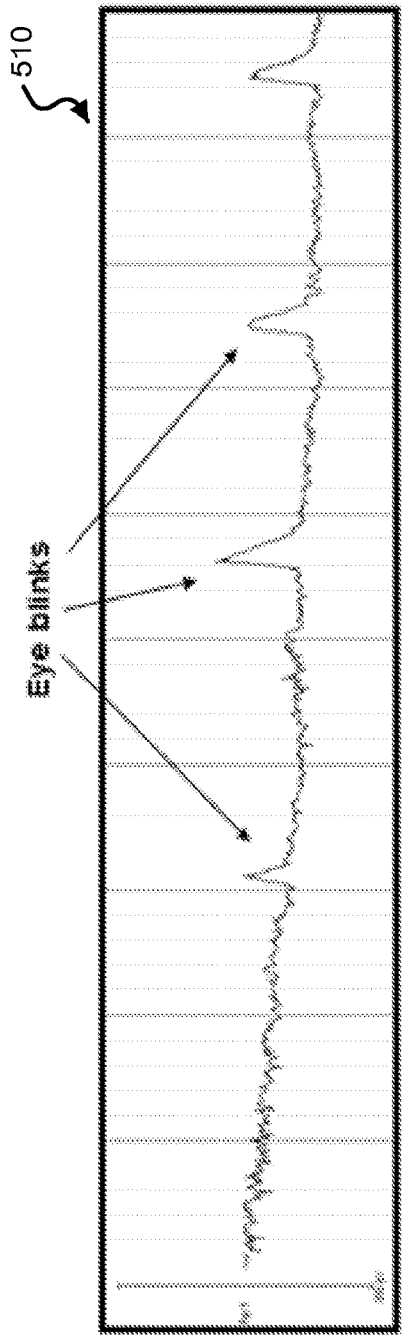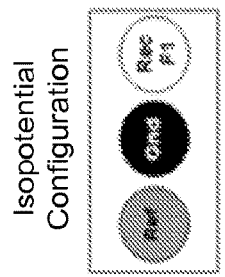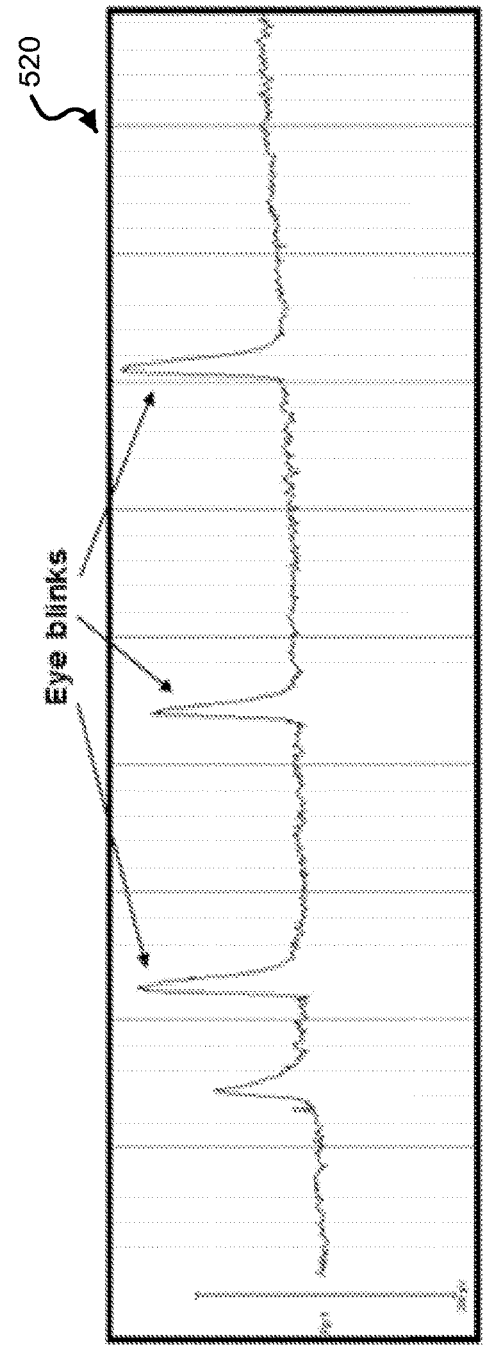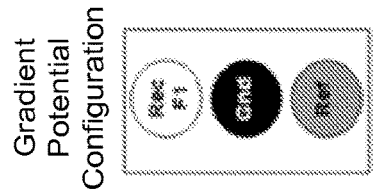
FIG. 5

CONFIGURATION AND SPATIAL PLACEMENT OF FRONTAL ELECTRODE SENSORS TO DETECT PHYSIOLOGICAL SIGNALS

CROSS-REFERENCE TO RELATED APPLICATIONS

This patent document is a 35 USC § 371 National Stage application of International Application No. PCT/US2013/064892, entitled "CONFIGURATION AND SPATIAL PLACEMENT OF FRONTAL ELECTRODE SENSORS TO DETECT PHYSIOLOGICAL SIGNALS," filed Oct. 14, 2013, which claims the benefit of priority of U.S. Provisional Patent Application No. 61/713,339, entitled "METHOD AND APPARATUS FOR OPTIMIZING CONFIGURATION AND SPATIAL PLACEMENT OF FRONTAL ELECTRODE SENSORS TO DETECT EEG BRAIN SIGNALS OF INTEREST", filed on Oct. 12, 2012. The entire content of the aforementioned patent applications are incorporated by reference as part of the disclosure of this application.

TECHNICAL FIELD

This patent document relates to systems, devices, and processes for acquiring and analyzing physiological signals.

BACKGROUND

Electroencephalography (EEG) is the recording of electrical activity exhibited by the brain using electrodes positioned on a subject's scalp, forming a spectral content of neural signal oscillations that comprise an EEG data set. For example, the electrical activity of the brain that is detected by EEG techniques can include voltage fluctuations, e.g., resulting from ionic current flows within the neurons of the brain. In some contexts, EEG refers to the recording of the brain's spontaneous electrical activity over a short period of time, e.g., less than an hour. EEG can be used in clinical diagnostic applications including epilepsy, coma, encephalopathies, brain death, and other diseases and defects, as well as in studies of sleep and sleep disorders. In some instances, EEG has been used for the diagnosis of tumors, stroke and other focal brain disorders.

One example of an EEG technique includes recording of event-related potentials (ERPs), which refer to EEG recorded brain responses that are correlated with a given event (e.g., simple stimulation and complex processes). For example, an ERP includes an electrical brain response—a brain wave—related to the sensory, motor, and/or cognitive processing. ERPs are associated with brain measures of perception (e.g., visual, auditory, etc.) and cognition (e.g., attention, language, decision making, etc.). A typical ERP waveform includes a temporal evolution of positive and negative voltage deflections, termed components. For example, typical components are classified using a letter (N/P: negative/positive) and a number (indicating the latency, in milliseconds from the stimulus event), for which this component arises.

SUMMARY

Devices, systems, and techniques are disclosed for acquiring physiological signals of interest using a limited quantity of electrode sensors, e.g., which can be used to determine cognitive and/or sensory performance, psychological states, and/or behavioral preferences.

In one aspect, a physiological sensor device includes a substrate formed of an electrically insulative material and structured to allow physical contact of the device with the frontal region of the head of a user, a first electrode configured at a first location on the substrate to acquire an electrophysiological signal of the user, a second electrode configured at a second location on the substrate to acquire a second electrophysiological signal of the user as a reference signal to the electrophysiological signal, and a third electrode configured on the substrate to acquire a third electrophysiological signal of the user as an electrical ground signal, in which the third electrode is configured at a third location at least partially between the first and the second locations on the substrate, and the first location is configured posterior to the second and third locations along a sagittal direction in the frontal region when the physiological sensor device is properly placed on the frontal region of the user, and in which the device is operable when electrically coupled to an electrical circuit to detect physiological signals of the user.

Implementations of the physiological sensor device can optionally include one or more of the following features. In some implementations of the device, for example, the first, second, and third electrodes can be linearly arranged on the substrate. For example, the detected physiological signals can be electroencephalography signals sensed from the brain of the user. In some examples, the detected electroencephalography signals can be associated with an event-related potential. For example, the detected physiological signals can be electromyography signals sensed from head muscles of the user associated with the user's eye blinking or facial expressions. In some implementations of the device, for example, the substrate can be formed of a mechanically flexible material structured to adhere to skin or a wearable item of the user. In some implementations, for example, the device can further include electrical interface components formed separately on the substrate and electrically coupled to the first, second, and third electrodes, respectively, via electrically conductive conduits, in which the electrical circuit is an external electrical circuit electrically coupled to the electrical interface components via wires. In some implementations, for example, the electrical circuit can include a signal processing circuit formed on the exemplary mechanically flexible substrate in electrical communication with the first, second, and third electrodes via electrically conductive conduits, in which the signal processing circuit can amplify the acquired physiological signals. For example, the electrical circuit can include a transmitter unit on the substrate in electrical communication with the signal processing circuit to transmit the amplified physiological signals to at least one of a data processing unit or a remote computer system. In some implementations, for example, the device can further include a power supply module electrically coupled to the electrical circuit to provide electrical power to the transmitter unit. In some examples, the physiological sensor device can be configured as a wearable patch worn on the user's scalp. In some examples, the physiological sensor device can be configured in a region of the wearable item capable of physical contact with the user's scalp. In some implementations, for example, the device can further include a fourth electrode configured at a fourth location on the substrate to acquire a second electrophysiological signal of the user, and a fifth electrode configured at a fifth location on the substrate to acquire a third electrophysiological signal of the user, in which the fourth location is configured left of the first location, and the fifth location is configured right of the first location.

In some implementations of the physiological sensor device, for example, the device is implemented in a system to provide a cognitive or sensory assessment. The system can include a data processing system in communication with the physiological sensor device and structured to include one or more memory units and one or more processors configured to process the detected physiological signals as physiological data to generate an information set including one or more quantitative values associated with a cognitive-sensory profile category indicative of one or more aspects of cognitive or sensory functions. For example, the one or more processors of the data processing unit can be configured to process the physiological signals detected by the physiological sensor device to generate the information set by selecting time intervals of interest within the physiological data based on the presented stimuli and the cognitive-sensory profile category, grouping, into one or more grouped data sets, the physiological data corresponding to the selected time intervals of interest, and providing a statistical measure of a relationship across or within the grouped data sets to generate the one or more quantitative values. For example, the one or more quantitative values can include a quantitative score depicting a level of one or both of cognitive and sensory performance based on at least one of the user's attention, memory, learning ability, confabulation characteristics, pattern integration ability, semantic integration ability, target detection ability, emotional valence, preference, or awareness, and wherein the quantitative score depicts the level at a particular time. In some implementations, the system can further include a stimulus delivery device to produce a sequence of stimuli based on the cognitive-sensory profile category that is presented to the user wearing the physiological sensor device, wherein the stimuli includes at least one of a visual, auditory, olfactory, tactile, or gustatory stimulating medium, in which the physiological sensor device is interfaced to the user to detect the physiological signals exhibited by the user before, during, and after a presentation of the sequence of stimuli. In some implementations, the data processing system can include a local computer proximate to and in communication with the physiological sensor device to receive the detected physiological signals from the physiological sensor device, the local computer configured to conduct initial processing of the detected physiological signals to produce initial physiological signal data, and a remote computer in communication with the local computer via a communication network or link to receive the initial physiological signal data from the local computer and to process the initial physiological signal data to generate the information set including one or more quantitative values associated with the cognitive-sensory profile category. For example, the local computer can be a mobile communications device including a smartphone or tablet that is in wireless communications with the physiological sensor device.

In another aspect, a method to provide a cognitive or sensory assessment of a subject includes acquiring electrophysiological signals of the subject from the frontal region of the subject's head to produce physiological data using a sensor device, and processing the physiological data to generate an information set including one or more quantitative values associated with a cognitive-sensory profile category indicative of one or more aspects of cognitive or sensory functions, in which the sensor device includes a substrate formed of an electrically insulative material and structured to allow physical contact of the sensor device with the frontal region of the head of the subject, and three electrodes including a recording electrode, a reference electrode, and a ground electrode to acquire the electrophysiological signals of the subject from three respective positions arranged on the substrate along the sagittal direction of the frontal region, in which the recording electrode is configured posterior to the ground and reference electrodes, and the ground electrode is configured between the recording and reference electrodes.

BRIEF DESCRIPTION OF THE DRAWINGS

FIG. 5 shows data plots of an exemplary EEG online recording using the exemplary rigid electrodes before stimuli presentation for both gradient potential and isopotential configurations.

DETAILED DESCRIPTION

Figure 1A:
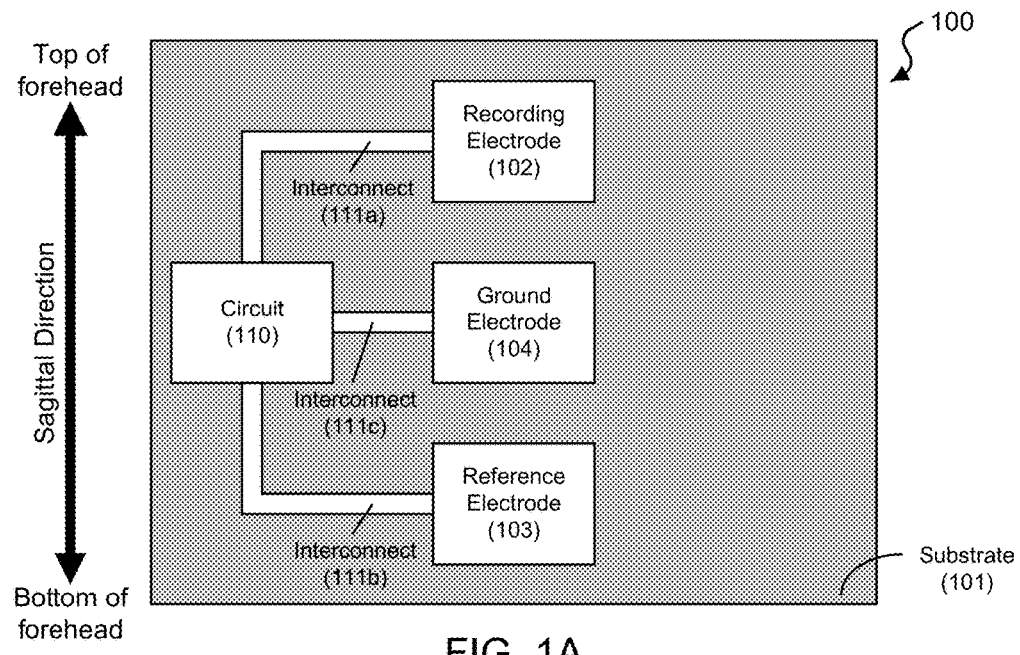
FIGS. 1A and 1B show block diagrams of an exemplary frontal electrode physiological sensor device of the disclosed technology.

Establishing reliable correlations between one's brain signals and the associated cognitive/psychological states (e.g., thoughts) can provide valuable and desired applications for clinic and other uses. Such correlations, extensively explored in fundamental sciences, have been the focus of various translational attempts into specialized applications such as assessment of cognitive impairment and enabling the physically impaired to communicate.

Some systems to characterize cognitive and psychological states have relied upon various behavioral and brain imaging techniques, e.g., such as functional resonance magnetic imaging (fMRI) and electroencephalography. For example, fMRI is an indirect measure of brain function by correlated metabolic function (e.g., oxygen consumption in the blood flow), whereas EEG is a direct measure of brain activity by recording changes of the electrical fields present at the scalp, deriving from electrical activity produced by neural cells.

There are several important factors in determining sensory and/or cognitive information about a subject. For example, such factors can include the type of stimuli that can evoke a subject's response, duration of the stimuli, inter-stimuli interval, number of repetitions of each presentation of stimuli, the levels of the stimuli (e.g., sound, brightness or contrast levels, etc.), markers associated with the onset of presentation of each stimuli, etc., as well as the recording sensors and systems. Also, the physiological parameter(s) of use (e.g., voltage, power, frequency, etc.), the related time window for analysis, and the analysis structure can affect the brain signal recordings and correlated cognitive evaluation. Deviations or mistakes from one or multiple of these parameters can make the difference between a useful or artifact driven, useless method.

Some traditional EEG recording techniques include an EEG cap covering the whole scalp, e.g., placed over the hair. These full cap EEG systems are typically neither comfortable nor aesthetically pleasing, and in some cases require the use of conductive gel, which is cumbersome to the user, and may require technical application, etc. Some EEG recording techniques do not utilize a full cap, but nonetheless include skin-mounted electrodes along with other electrodes that are spatially disparate and require a bulky headset that is not efficient in terms of portability and comfort, and/or such skin-mounted electrode systems suffer from poor signal quality revealing inadequate signal to noise ratio to optimal detection of ERPs. For example, one class of skin-mounted electronics systems used an electrode configuration having frontal electrodes and non-frontal electrodes (e.g., some placed behind the subject's ears) to acquire muscular and brain signals, but with signal resolution only able to extract coarse muscular and brain signals that included eye blink and alpha rhythm oscillations when the subject's eyes were closed, and thus incapable to adequately detect finer brain signals, such as ERPs. These techniques are either cumbersome or unable to acquire relevant brain signals to extract relevant brain signals reflective of behavioral and brain measures of interest, e.g., for characterization of cognitive and/or psychological states.

For example, measurements of event-related potentials for sensory, motor and/or cognitive analysis can include techniques that capitalize in measuring transient electric shifts (e.g., ERP components) that are time-locked to the onset of a presented stimulus (e.g., visual, auditory, olfactory, gustatory, or tactile) and reflect the underlying brain activity during the investigated neuropsychological process. For example, ERP components can be indicative of multiple sensory, motor and cognitive functions. The amplitude modulation and scalp distribution of a variety of ERPs represent reliable and effective brain markers for normal neuropsychological processing of a wide range of cognitive operations. Moreover, abnormal modulation and latencies of ERPs have been associated with various sensory and cognitive deficits linked to neuropsychiatric disorders, such as schizophrenia, Alzheimer's and Parkinson's.

As such, the use of these measures of brain activity is of great value to biomedical research and development and clinical applications of effective diagnostic tools for neurological and neuropsychiatric disorders. However, today's use of ERP brain markers is still confined to sophisticated laboratory settings and medical facilities. Moreover, traditional methods to record EEG signals are clunky, cumbersome, and unable to be used effectively in general purpose environments.

Devices, systems, and methods are disclosed for acquiring physiological signals of interest using a limited quantity of electrode sensors, e.g., which can be used to determine cognitive and/or sensory performance, psychological states, and/or behavioral preferences.

In one aspect, a physiological sensor device includes a substrate formed of an electrically insulative material and structured to allow physical contact of the physiological sensor device with the frontal region of the head of the user, and, an optimal configuration of three electrodes on the substrate providing a minimized device footprint when the device is properly applied on the user's forehead. The three electrodes include a recording electrode, a reference electrode, and a ground electrode to acquire the electrophysiological signals of the subject from three respective positions arranged on the substrate along the sagittal direction of the frontal region, in which the recording electrode is configured posterior to the ground and reference electrodes, and the ground electrode is configured between the recording and reference electrodes.

The disclosed technology integrates advanced cognitive neuroscience, neurophysiology, psychology and electromagnetics in optimal configurations of physiological signal detection electrodes frontally placed on the forehead to enable individual or group evaluation of a variety of cognitive aspects and physiological/health monitoring, e.g., including but not limited to, evaluation of cognitive state, knowledge, learning mechanisms, behavioral preferences, vulnerability and/or symptoms of neurological and neuropsychiatric pathologies. The disclosed technology can be implemented in devices that provide easy and user-friendly operation, portability, and comfort, thereby permitting real-world usage and systematic health monitoring. Additionally, for example, the disclosed technology can be used in a variety of health, education, entertainment, and marketing applications.

For example, the disclosed technology includes physiological sensor devices and methods using frontal EEG recording electrodes located on a user's forehead for versatile, rapid, and non-obtrusive physiological data acquisition (e.g., including brain signal monitoring) that do not overlap with hair. For example, in some implementations, the exemplary physiological sensor devices are configured to a small size and can be formed with a variety of different materials (e.g., which can be tailored for specific applications), such that the devices may be easily applied, barely or not even felt by the user, or seen by others. For example, application and operation of such devices can be performed by the user, e.g., following simple instructions, without any need for technical expertise to apply or operate the device or system. This can significantly mitigate problems present in existing systems including the need of technical expertise for operation and lack of comfort and portability of sensor devices.

For example, the disclosed systems can be used by general users outside a clinical setting, with safety and accuracy, allowing for the freedom to use in a wide variety of contexts and locations, significantly reducing the cost and requirements of use for brain monitoring systems. The disclosed devices and methods can be effectively used by non-experts to place the exemplary frontal electrode sensor device on the forehead of evaluated persons (or even allow the subjects to place the frontal electrodes on themselves) to optimally extract brain signals, e.g., which in some implementations can be associated with event-related potentials (ERPs), and to provide a cognitive and/or sensory profile of the subject or subjects. For example, such non-expert users need not be neuroscientists, psychologists, nor specialized physicians to implement the physiological data acquisition or interpret the generated cognitive and/or sensory profile information of the user provided by the analysis of the acquired physiological data. For example, the non-expert users can implement the disclosed systems and methods to obtain awareness and mental information profiles of the evaluated person(s), e.g., either themselves or others. Additionally, for example, implementations of the disclosed devices, systems and methods can also be used within the context of brain-machine interfaces and expands the possible applications of such systems.

In some aspects, the disclosed technology includes techniques for designing an optimal sensor configuration for frontal electrode placement on a subject's forehead to accurately detect brain event-related potentials. In some examples, the techniques can use information from specific stimuli presentation paradigms (e.g., sensory stimulation can include visual, auditory, olfactory, gustatory or somatosensory cues) and relate the presented stimuli with recorded brain electrophysiological signals (e.g., EEG) in specific temporal windows (e.g., based on physiology data related to the neuropsychological mechanisms underlying ERPs) and spatial regions (e.g., based on neuroanatomy and on scalp topographic voltage mapping and neural generators source analysis) of interest.

Exemplary Embodiments of the Disclosed Devices, Systems, and Methods

In one exemplary embodiment, a physiological sensor device of the present technology includes a substrate that is formed of an electrically insulative material and structured to allow physical contact of the device with the frontal region of the head of a user, a recording electrode configured at a first location on the substrate to acquire an electrophysiological signal of the user, a reference electrode configured at a second location on the substrate to acquire a second electrophysiological signal of the user as a reference signal to the electrophysiological signal; and a ground electrode configured at a third location on the substrate to acquire a third electrophysiological signal of the user as an electrical ground signal. The physiological sensor device is configured such that the first electrode is configured posterior to the third and second electrodes along a sagittal direction in the frontal region, and the third electrode is positioned at least partially between the first and the second locations on the substrate. The physiological sensor device is operable when electrically coupled to an electrical circuit to detect physiological signals of the user.

In some implementations of the exemplary frontal electrode physiological sensor device, the recording electrode, the ground electrode, and the reference electrode are linearly arranged on the substrate. For example, the arrangements of the three electrodes can be aligned in a substantially straight line along the sagittal direction of the frontal region of the user's head, with the recording electrode (e.g., at the first position) posteriorly positioned to the ground electrode, which is posteriorly positioned to the reference electrode.

In some implementations, for example, the physiological signals detected by the exemplary frontal electrode physiological sensor device can be electroencephalography (EEG) signals sensed from the brain of the user. For example, the EEG signals can be associated with an event-related potential, e.g., based on a stimulus presented to the user wearing the device on the frontal region of the user's head. In other implementations, for example, the physiological signals detected by the exemplary frontal electrode physiological sensor device can be electromyography (EMG) signals sensed from head muscles (e.g., including facial muscles) of the user. For example, the EMG signals can be resultant from eye blinks of the user in response to an event-related potential, e.g., based on a stimulus presented to the user wearing the device on the frontal region of the user's head.

In some embodiments, for example, the exemplary frontal electrode physiological sensor device can include electrical interface components (e.g., electrical contact pads) formed separately on the substrate and electrically coupled to the recording, ground, and reference electrodes, e.g., via electrically conductive conduits, in which the electrical interface components provide an electrical coupling site to be connected (e.g., via wires) to an external electrical circuit, e.g., electrical signal amplifier and/or processing unit.

In some embodiments, for example, the exemplary frontal electrode physiological sensor device can include (i) electrical circuits for signal amplification/processing and (ii) a transmitter unit, all on the mechanically flexible substrate in electrical communication with the recording, ground, and reference electrodes, e.g., via electrically conductive conduits. In this embodiment, the sensor device is configured to record the physiological signals, amplify and process them, and transmit the recorded physiological signals to a remote device, e.g., further electrical signal processing unit, such as an amplifier, and/or a computer system. Also, for example, the exemplary frontal electrode physiological sensor device can include a power supply module electrically coupled to the transmitter unit to provide electrical power to the transmitter unit.

In some embodiments, for example, the exemplary frontal electrode physiological sensor device can include one or more recording electrodes configured on the substrate to acquire multiple channels of electrophysiological signals of the user. For example, the exemplary frontal electrode physiological sensor device can include two additional recording electrodes (in which the device includes five electrodes: three recording electrodes, one reference electrode, and one ground electrode), in which the additional recording electrodes are proximate to the first recording electrode, ground electrode, and reference electrode arranged in the sagittal direction. In this example, the two additional electrodes can be linearly arranged in the same or similar sagittal direction as the first recording electrode. In other examples, some of the additional electrodes can be positioned to the left of the first recording electrode, while others additional recording electrode can be positioned to the right of the first recording electrode.

In some implementations, for example, the exemplary frontal electrode physiological sensor device is configured as an epidermal electronic sensor (EES) device in which the substrate is formed of a mechanically flexible and/or stretchable material structured to mechanically conform to and/or adhere to the skin or a wearable item of the user. In some examples of an epidermal physiological sensor device of the present technology, the device can include ultrathin silicon islands interconnected by serpentine-like wires that all rest on a biologically inert flexible polymer. In some implementations, for example, the epidermal physiological sensor device can include a processing unit configured on the flexible substrate and structured to include transistors, capacitors, resistors, inductors, and/and other circuit elements, etc., to process the electrophysiological signals acquired by the electrodes. In some implementations, for example, the processing unit of the epidermal physiological sensor device can include a processor and a memory unit. The epidermal physiological sensor device can be configured to have a thickness approximate to that of a human hair.

FIG. 1A shows a block diagram of an exemplary embodiment of a frontal electrode sensor device 100 capable to acquire electrophysiological signals from the frontal region of the head of a subject. The device 100 includes a substrate 101 of an electrically insulative material, which, in some device implementations, can be made of a mechanically flexible material. In some examples, the substrate 101 can include polydimethylsiloxane (PDMS), thin polyurethane with acrylic adhesive, or polyvinyl alcohol (PVA), among others. The frontal electrode sensor device 100 includes a three-electrode configuration, including a recording electrode 102, a reference electrode 103, and a ground electrode 104 configured between the recording electrode 102 and the reference electrode 103 on the basal side of the substrate 101 (e.g., the detection side of the device 100 that is in contact with the skin of the user). The electrodes of the device 100 are configured along a sagittal direction in the frontal region such that the recording electrode 102 is positioned posteriorly to the ground electrode 104, which is positioned posteriorly to the reference electrode 103. The ground electrode 104 is positioned at least partially between the recording electrode 102 and the reference electrode 103 on the substrate 101. This recording-ground-reference electrode arrangement on the frontal region of the user's head or forehead region can minimize the overall footprint of the electrodes of the frontal electrode sensor device 100, a significant benefit for such sensor devices. This recording-ground-reference electrode arrangement also provides good signal isolation between the recording electrode and the reference electrode, thus enabling more sensitive and high quality signal recording operation. The general alignment of the electrodes in the sagittal direction, rather than the horizontal direction that is perpendicular to the sagittal direction, is a notable feature of this recording-ground-reference electrode arrangement and can provide beneficial sensing operations with respect to acquiring various cognitive/psychological state signals with desired accuracy.

In some embodiments of the device 100, for example, the recording electrode 102, the ground electrode 104, and the reference electrode 103 are linearly arranged on the substrate 101. For example, the arrangements of the three electrodes can be aligned in a substantially straight line along the sagittal direction, with the recording electrode. In other embodiments of the device 100, for example, the three electrodes can be arranged in a nonlinear alignment that includes the recording electrode 102 positioned posteriorly to the ground electrode 104 that is positioned posteriorly to the reference electrode 103, with the ground electrode 104 at least partially between the recording electrode 102 and the reference electrode 103 on the substrate 101.

The frontal electrode sensor device 100 is operable to acquire electrophysiological data when electrically coupled to an electrical circuit. In the exemplary embodiment shown in FIG. 1A, the frontal electrode sensor device 100 includes an electrical circuit 110 on the substrate 101 electrically coupled to the recording electrode 102, the reference electrode 103, and the ground electrode 104 via individual electrical interconnects 111a, 111b, and 111c, respectively. In some embodiments, for example, the electrical circuit 110 can include a transmitter unit in electrical communication with each of the electrodes 102, 103, and 104, e.g., via the electrically conductive conduits 111a, 111b, and 111c, respectively. In this embodiment, the device 100 can record the physiological signals and transmit the recorded physiological signals to a remote electrical signal processing unit, e.g., such as an amplifier, and/or a computer system. Also, for example, the electrical circuit 110 can include a power supply module electrically coupled to the transmitter unit to provide electrical power to the transmitter unit.

Figure 1B:
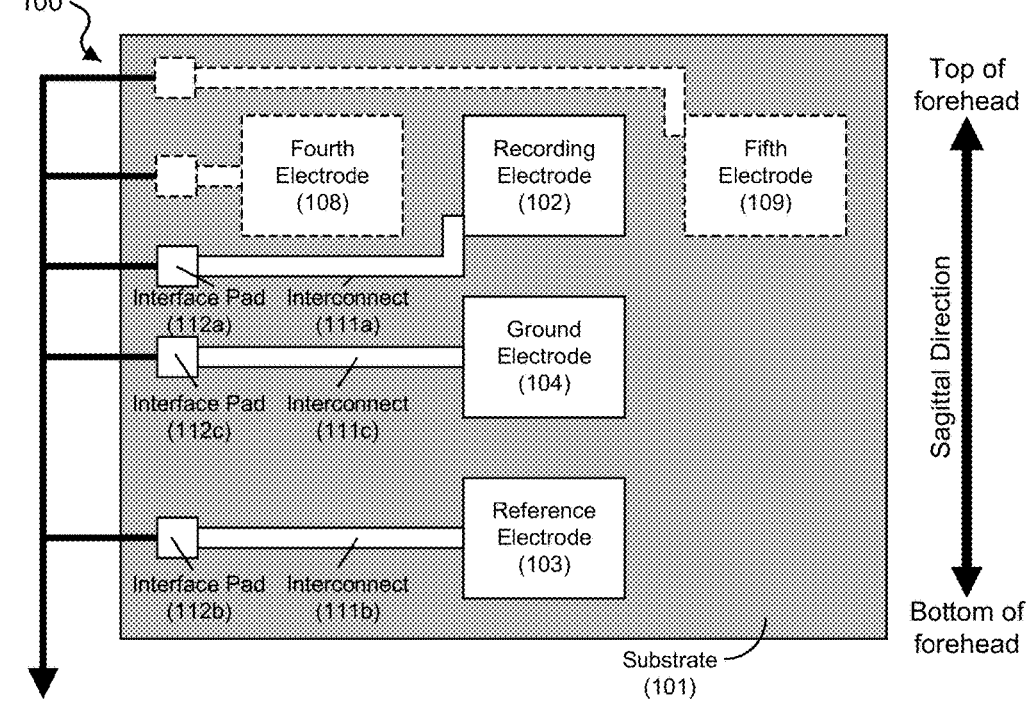

In some embodiments, for example, as shown in FIG. 1B, the frontal electrode sensor device 100 can include electrically conductive interface (contact) pads 112a, 112b, and 112c coupled to the interconnects 111a, 111b, and 111c, respectively, to provide a conductive surface to electrically interface an external electrical circuit to the electrodes 102, 103, and 104 of the device 100. For example, the external electrical circuit can be an electrical signal processing unit, e.g., such as a signal amplifier, and/or a computer system. In some embodiments, for example, as shown in FIG. 1B, the frontal electrode sensor device 100 can optionally include a fourth electrode 108 configured at a fourth location on the substrate 101 to the left of the recording electrode 102 to acquire a second EEG signal of the user; and a fifth electrode 109 configured at a fifth location on the substrate 101 to the right of the recording electrode 102 to acquire a third EEG signal of the user.

For example, the acquired recording, reference, and ground signals are received by the signal processing unit that processes the acquired signals in a differential amplifier to amplify the difference between the recording and reference electrophysiological signals. The ground signals recorded by the device 100 (via the ground electrode 104) can be connected to the ground channel of the exemplary differential amplifier, e.g., to synchronize the signal parameters between the device 100 and the amplifier. For example, the ground electrode 104 can minimize leakage currents that may flow through the subjects via the recording system, and thus decrease any artifacts. For example, the ground electrode 104, when electrically coupled to an electrical circuit (e.g., such as the external electrical circuit), need not be connected to the ground of the electrical circuit. Alternative roles of the ground electrode can include serving as an electrode for actively canceling interference. For example, the ground electrode can be electrically connected to a "driven right leg" feedback circuit, e.g., which is used in some biological signal amplification systems that measure very small electrical signals emitted by the body (e.g., EEG, EMG, ECG). For example, the frontal electrode sensor device 100 can acquire referential recordings of electrophysiological signals at the frontal region. The position of the reference electrode 103, as well as its spacing with respect to the recording electrode 102 (or, in some implementations, other recording electrodes in addition to the recording electrode 102) is important, since the recordings of interest will be determined by a comparison of the activity recorded by the recording electrode 102 with respect to the activity recorded by the reference electrode 103. For example, if such signals were the same, then the detected signal reading would be zero. From this perspective, for example, one could position the recording electrode 102 at a site that will allow for detection of the physiological signal of interest and position the reference electrode 103 at a substantial distance away from it at a site that will not capture the physiological signal of interest (or show a significant reduction of the signal of interest). However, this presents a challenge that becomes greater when it is important to minimize the footprint of the device 100 (e.g., the occupied spatial area or "real estate" by the whole array of electrodes) on the forehead. For example, in the examples shown in FIGS. 1A and 1B, the electrodes 102, 103, and 104 are positioned and spaced in such a manner that the signals captured are significantly different, and thereby relevant, as well as occupy a minimal total area occupied by electrodes 102, 103, and 104. Methods are described in this patent document to determine optimal configurations of location and spacing are complex and can integrate psychological, neurophysiological and engineering principles. In the example shown in FIGS. 1A and 1B, the position of the reference electrode 103 is located in a substantially linear alignment with respect to the recording electrode 102, and both electrodes 102 and 103 and the ground electrode 104 are also arranged on a mid-sagittal line through the center of the frontal region, in this example. The signal-processed signals are provided as physiological data, which can subsequently be processed to provide a cognitive and/or sensory profile.

In some implementations, the device 100 can be configured as an epidermal electronics physiological sensor device that can be worn directly on skin or a wearable item in contact with the frontal region. In some implementations, for example, the device 100 can include an additional electrically insulative layer or layers, e.g., configured on the apical side of the device 100 (e.g., the non-detection side, not in contact with the skin of the user). The additional layer(s) can provide further support for the device 100. In some examples, the additional layer(s) can include various artistic designs, such that, when worn by the user directly on the user's skin, the device 100 can also serve as a (temporary) tattoo.

In some implementations, the device 100 can be included in a system to provide a cognitive or sensory assessment of the user. Some examples of such systems are provided in the system. PCT Patent Application PCT/US13/62491, entitled "SYSTEMS AND METHODS FOR SENSORY AND COGNITIVE PROFILING," filed Sep. 27, 2013, of which the entire contents are incorporated by reference for all purposes as part of the disclosure of this patent document.

Figure 1C:
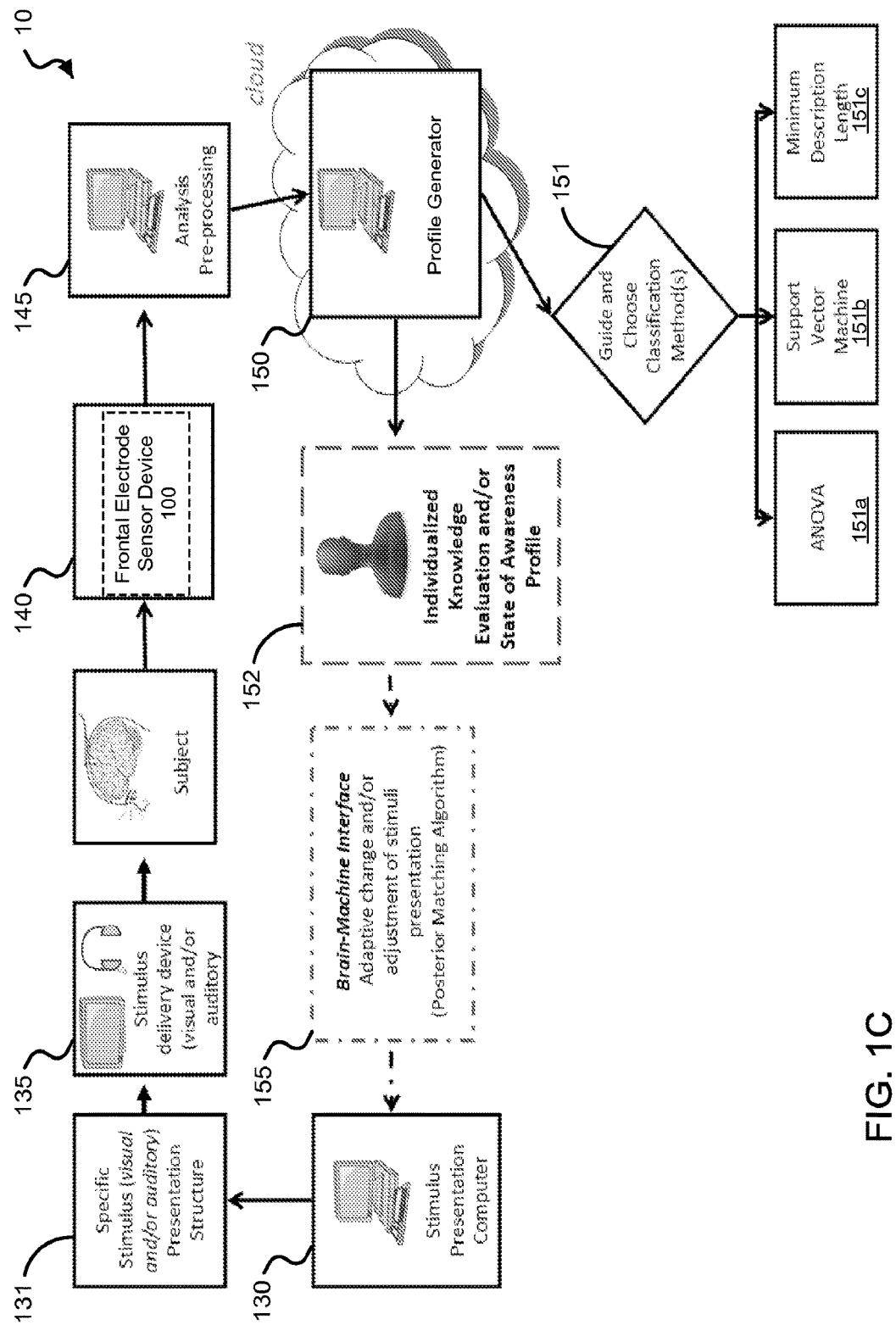
FIG. 1C shows a diagram of an exemplary system of the disclosed technology for acquisition, analysis, and evaluation of physiological signals to produce an individual or group knowledge and/or state of awareness profile.

An exemplary modular system including the frontal electrode sensor device 100 of the disclosed technology for acquisition, analysis and evaluation of physiological signals to produce an individual or group cognitive and/or sensory profile is shown in FIG. 1C. For example, the system can be implemented to provide a cognitive performance profile, a sensory performance profile, and a cognitive and sensory performance profile indicative of a subject's cognitive and/or sensory ability at the time of the assessment. For example, the type of cognitive and/or sensory profile can be selected by the user (e.g., such as the subject or a system operator) to provide a set of information including a quantitative level of cognitive and/or sensory performance, e.g., including, but not limited to, attention, memory, learning, confabulation, pattern integration, semantic integration, target detection, emotional valence, preference, and state of awareness. The system allows an operator to select the type of profile to be produced. In some implementations, the system can be implemented to provide the cognitive and/or sensory profile using only physiological data acquired from the subject, e.g., with no overt behavioral response elicited from the subject. In some implementations, the system can be implemented to provide the cognitive and/or sensory profile including previously acquired physiological data from the subject, or other subjects (e.g., group data). The system can thereby, for example, be implemented to provide a cognitive and/or sensory profile about a group. FIG. 1C shows a diagram of an exemplary system 10 configured to include independent modular units or devices that can be configured in a variety of different embodiments.

The system 10 includes a stimulus presentation module 130 to configure a specific stimulus presentation structure 131 to effectuate a presentation of a stimulus or a sequence of stimuli to a subject. In some examples, the stimulus presentation module 130 is embodied in a computing device, e.g., including a processor and memory unit. For example, the stimuli can include any stimulus type, including a visual, auditory, olfactory, tactile, and/or gustatory stimulating medium. Examples of visual stimuli can include images, written words, etc. Examples of auditory stimuli can include spoken words, animal vocalizations, synthesized sounds, etc. The specific stimulus presentation structure 131 can be configured to include, but is not limited to, a particular type or types of stimuli, the duration of presentation of the stimuli, an inter-stimuli interval, a number of repetitions (if any) of each presentation, magnitude and/or frequency parameters associated with type of stimuli (e.g., intensity of sound or brightness or contrast level of light), a digital marker associated with the presentation of each stimuli, and a label or category of the stimuli (e.g., target or non-target).

The system 10 can include a stimulus delivery module 135 in communication with the stimulus presentation module 130 to present the stimulus or the sequence of stimuli to the subject, e.g., based on the stimulus presentation structure 131. For example, the stimulus delivery module 135 can include at least one of a visual display, an auditory speaker, and an actuator to provide an olfactory, tactile, and/or gustatory stimulus. In some implementations, for example, the stimulus presentation module 130 and the stimulus delivery module 135 can be configured in the same device, e.g., such as a computer or mobile communication and/or computing device.

The system 10 includes a physiological data acquisition module 140, which can be embodied as the frontal electrode sensor device 100, to acquire physiological signals of the subject before, during, and/or after the presentation of the stimuli or sequence of stimuli via the stimulus delivery module 135. For example, the frontal electrode sensor device 100 can be implemented to acquire electrophysiological signals from the subject, e.g., including, but is not limited to, electroencephalography (EEG) signal data and electromyography (EMG) signal data. In some implementations, for example, the frontal electrode sensor device 100 can include electrophysiological sensing electrodes, e.g., EEG and/or EMG electrodes, or other types of electrophysiological sensing electrodes, coupled to a signal acquisition device, e.g., such as an analog or digital amplifier coupled to a memory.

In some embodiments, for example, the frontal electrode sensor device 100 can be configured in a standard EEG system with rigid electrodes attached to a cap worn by the subject. In some embodiments, for example, the frontal electrode sensor device 100 can be configured in a portable EEG system using flexible electronics that can be worn on the subject, e.g., directly applied the subject's skin or worn in a wearable item (e.g., such as a hat) by the subject with the frontal electrode sensor device 100 in physical contact with the frontal region of the subject's scalp. For example, the frontal electrode sensor device 100 can be configured in a standard EMG system with rigid electrode or a portable EMG system using flexible electronics that can be worn on the subject, in which the frontal electrode sensor device 100 is in physical contact with the frontal region of the subject's scalp. In this exemplary configuration, the frontal electrode sensor device 100 in the rigid electrode standard EMG system or portable flexible electronics EMG system is capable of detecting movements that can be associated with drowsiness or facial expressions of the subject.

The system 10 includes an analysis pre-processing module 145 to receive the acquired physiological signals as data, and in some implementations, to perform pre-processing analysis techniques on the acquired data. For example, the analysis pre-processing module 145 can be implemented to identify exemplary onset markers in the acquired electrophysiological data (e.g., EEG data), segment the electrophysiological data, filter raw signal data to increase signal to noise, etc. In some implementations, for example, the analysis pre-processing 145 can be embodied in a computer device in communication with the exemplary device 100. In some implementations, for example, the analysis pre-processing module 145 can be configured in the same exemplary device that embodies the physiological acquisition module 140 (e.g., such as the frontal electrode sensor device 100).

The system 10 includes a profile generation module 150 to process the physiological data acquired by the frontal electrode sensor device 100 to provide a cognitive or sensory assessment of the subject, or in some examples, of a group. For example, the profile generation module 150 processes the physiological to generate an information set 152 that includes one or more quantitative values that are associated with the selected profile category, e.g., such as a knowledge evaluation or state of awareness profile. For example, the information set 152 provides more than a measure of psychological and neurophysiological natural events. For example, the profile can provide an individual (or group) assessment of one's (or group's) level of knowledge of specific issues (e.g., determination of a given person knowledge about a specific topic, event, learned skill or even preference) and/or state of conscious (or unconscious) awareness. In some implementations of the system 10, for example, the profile generation module 150 can also include processing behavioral signal data, e.g., acquired from the subject or group of individuals that include or do not include the subject, from a behavioral signal data acquisition module (not shown in FIG. 1C) to provide the cognitive or sensory assessment of the subject or of a group.

Figure 1D:
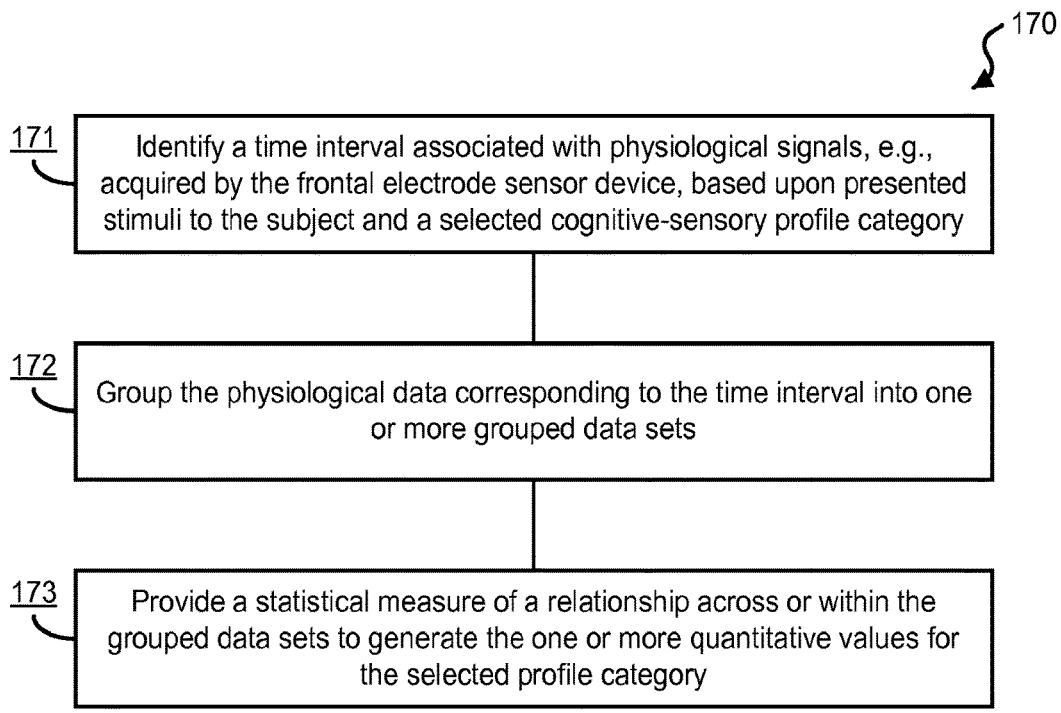
FIGS. 1D-1F show process diagrams of exemplary methods to generate a quantitative information set of an exemplary cognitive and/or sensory profile.

FIG. 1D shows a process diagram of an exemplary method 170 to generate the information set associated with the cognitive and/or sensory profile, e.g., implemented by the profile generation module 150, using the physiological data acquired by the exemplary frontal electrode sensor device 100. In some implementations, for example, the method 170 can also include using behavioral signal data acquired from the subject, or group of individuals that include or do not include the subject. The behavioral signal data can be processed in implementations of at least some or all of the processes of the method 170. The method 170 can include a process 171 to identify a time interval associated with the physiological signals (and/or behavioral signal data) based upon the presented stimuli and the selected profile category. For example, a time interval can include contiguous, discontinuous, continuous, discrete, or single time points. The method 170 can include a process 172 to group the data (e.g., physiological and/or behavioral) corresponding to the time interval into one or more grouped data sets. For example, the process 172 can include grouping the physiological data (and/or behavioral data) based on a pre-assigned category of the individual stimulus and/or an associative relationship of consecutive stimuli. The method 170 can include a process 173 to provide a statistical measure of a relationship across or within the grouped data sets to generate the one or more quantitative values for the selected profile category. In some implementations, for example, the method 170 can include a process to enhance the signal of the physiological (and/or behavioral data) in the grouped data sets.

Figure 1E:
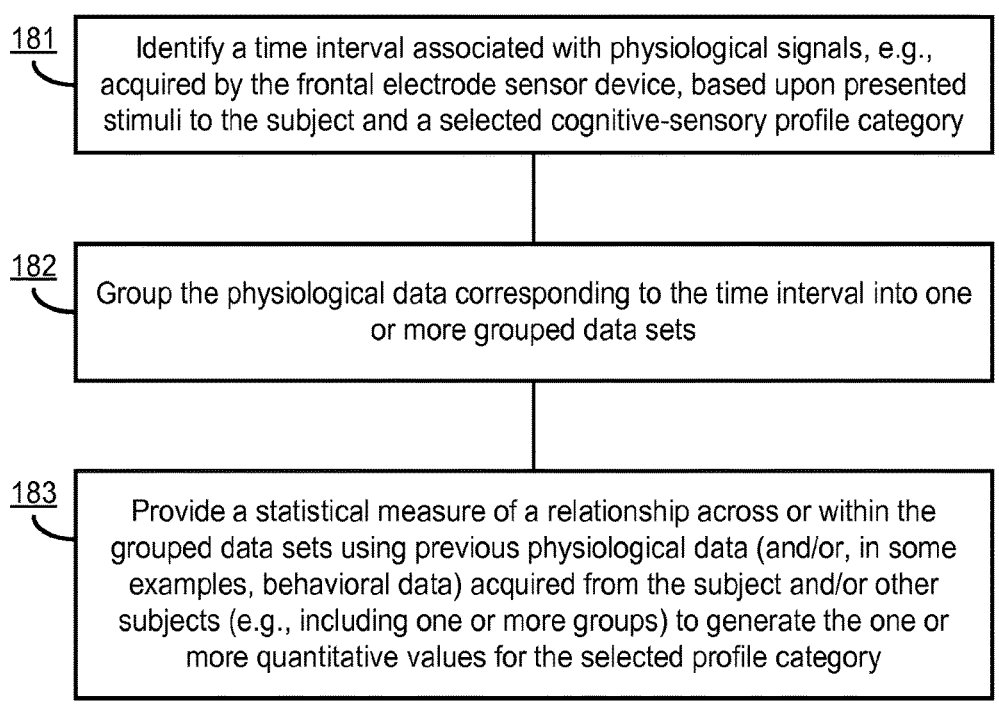

FIG. 1E shows a process diagram of an exemplary method 180 to generate the information set associated with the cognitive and/or sensory profile using previous individual and/or group information, e.g., implemented by the profile generation module 150, using the physiological data acquired by the exemplary frontal electrode sensor device 100. In some implementations, for example, the method 180 can also include using behavioral signal data acquired from the subject, or group of individuals that include or do not include the subject. The method 180 can include a process 181 to identify a time interval associated with the physiological signals (and/or behavioral signal data) based upon the presented stimuli and the selected profile category. The method 180 can include a process 182 to group the data, e.g., physiological data (and/or behavioral data), corresponding to the time interval into one or more grouped data sets. For example, the process 182 can include grouping the physiological data (and/or behavioral data) based on a pre-assigned category of the individual stimulus and/or an associative relationship of consecutive stimuli. The method 180 can include a process 182 to provide a statistical measure of a relationship across or within the grouped data sets using previous physiological data (and/or behavioral data) acquired from the subject and/or other subjects (e.g., including one or more groups) to generate the one or more quantitative values for the selected profile category.

Figure 1F:
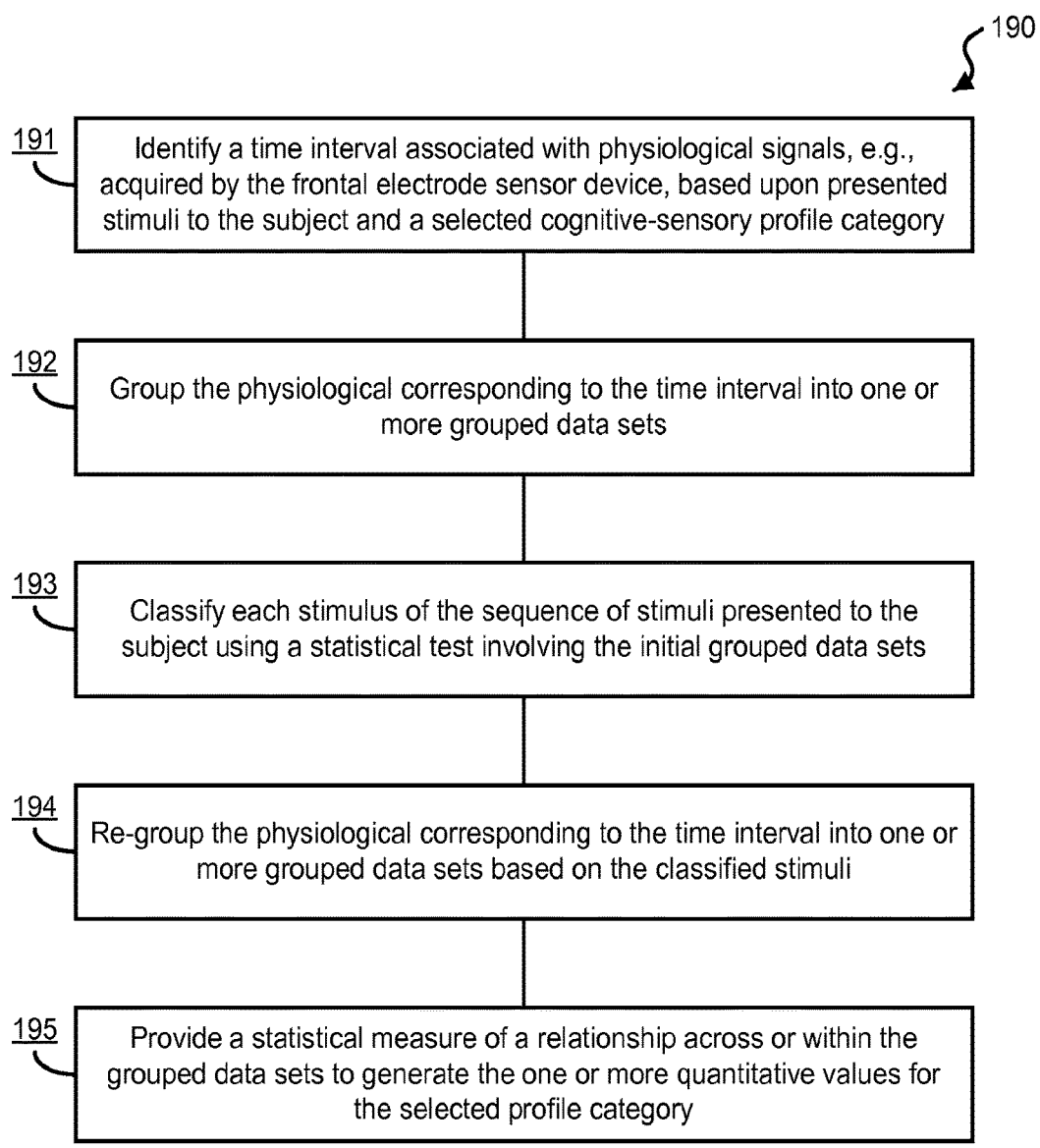

FIG. 1F shows a process diagram of an exemplary method 190 to generate the information set associated with the cognitive and/or sensory profile using a guided classification technique, e.g., implemented by the profile generation module 150, using the physiological data acquired by the exemplary frontal electrode sensor device 100. In some implementations, for example, the method 190 can also include using behavioral signal data acquired from the subject, or group of individuals that include or do not include the subject. The method 190 can include a process 191 to identify a time interval associated with the physiological signals (and/or behavioral signal data) based upon the presented stimuli and the selected profile category. The method 190 can include a process 192 to group the data, e.g., physiological data (and/or behavioral data) corresponding to the time interval into one or more initial grouped data sets. The method 190 can include a process 193 to classify each stimulus of the sequence of stimuli presented to the subject using a statistical test involving the initial grouped data sets. The method 190 can include a process 194 to re-group the physiological data (and/or behavioral data) corresponding to the time interval into one or more grouped data sets based on the classified stimuli. The method 190 can include a process 195 to provide a statistical measure of a relationship across or within the grouped data sets to generate the one or more quantitative values for the selected profile category.

In some examples, the profile generation module 150 can implement guided classification algorithms with context specific parameters to guide and choose from a variety of classification and statistical methods, e.g., including, but not limited to, ANOVA based techniques 151a, support vector machine based techniques 151b, and minimum description length techniques 151c, among others. In some implementations, the profile generation module 150 can be embodied on a computer system or communication network (referred to as 'the cloud') that includes one or more remote computational processing devices (e.g., servers in the cloud).

The system 10 can be configured to include a brain-machine interface module 155 to refine the generated cognitive and/or sensory profiles and/or actuate an interaction between a user and a machine. In one example, the brain-machine interface module 155 can provide a feedback delivery of a new stimulus or multiple stimuli to the stimulus presentation module 130 based on the cognitive and/or sensory profile of an individual subject or group subject that has been generated from the profile generation module 150, e.g., from an on-going implementation of the system 10 or a previously generated profile by the system 10. For example, the brain-machine interface module 155 can adaptively change or design stimuli paradigms that optimally extract information from the subject that is analytically processed to maximize a desired objective. For example, some implementations of the brain-machine interface module 155 can include, but are not limited to, assisted-learning and target detection applications.

In some implementations of the system 10, the profile generation module 150, the stimulus presentation module 130, the stimulus delivery module 135, and the brain-machine interface module 155 can be embodied in a single computing system, e.g., a desktop computer, a laptop computer, or a mobile communications device including a smart-phone or tablet, that interacts with the physiological data acquisition module 140 (e.g., the frontal electrode sensor device 100). In other implementations, the modules 150, 130, 135, and 155 can be configured in two or more computing devices in communication with each other and including various combinations of the modules 150, 130, 135, and 155. In some implementations, the system 10 can be configured to just include the physiological data acquisition module 140 and the profile generation module 150. In such exemplary implementations, the system 10 can use environmental stimuli (e.g., light, sounds, smells, tastes, and/or tactile contacts) that are presently available in the subject's surroundings.

In some aspects, a method to provide a cognitive or sensory assessment of a subject using the physiological sensor devices of the disclosed technology includes acquiring electrophysiological signals of the subject from the frontal region of the subject's head to produce physiological data using a sensor device, and processing the physiological data to generate an information set including one or more quantitative values associated with a cognitive-sensory profile category indicative of one or more aspects of cognitive or sensory functions. The sensor device includes a substrate formed of an electrically insulative material and structured to allow physical contact of the sensor device with the frontal region of the head of the subject, and three electrodes including a recording electrode, a reference electrode, and a ground electrode to acquire the electrophysiological signals of the subject from three respective positions arranged on the substrate along the sagittal direction of the frontal region, in which the recording electrode is configured posterior to the ground and reference electrodes, and the ground electrode is configured between the recording and reference electrodes.

In some implementations of the method to provide the cognitive and/or sensor assessment, for example, the method can further include presenting a sequence of stimuli to the subject, the sequence of stimuli based on the cognitive-sensory profile category, in which the acquiring the physiological signals is implemented before, during, and after the presenting the sequence of stimuli. In some implementations, for example, the method can further include selecting the cognitive-sensory profile category from among a cognitive performance profile, a sensory performance profile, and a cognitive and sensory performance profile. For example, the sequence of stimuli can include at least one of a visual, auditory, olfactory, tactile, or gustatory stimulating medium based on the selected cognitive-sensory profile category. For example, the one or more quantitative values can include a quantitative score depicting a level of one or both of cognitive and sensory performance based on at least one of the subject's attention, memory, learning ability, confabulation characteristics, pattern integration ability, semantic integration ability, target detection ability, emotional valence, preference, or awareness state, and wherein the quantitative score depicts the level at a particular time. In some implementations, for example, the method can further include identifying a time interval associated with the physiological signals based on the cognitive-sensory profile category, grouping the physiological data corresponding to the time interval into one or more grouped data sets, and providing a statistical measure of a relationship across or within the grouped data sets to generate the one or more quantitative values for the selected cognitive-sensory profile category.

Figure 1G:
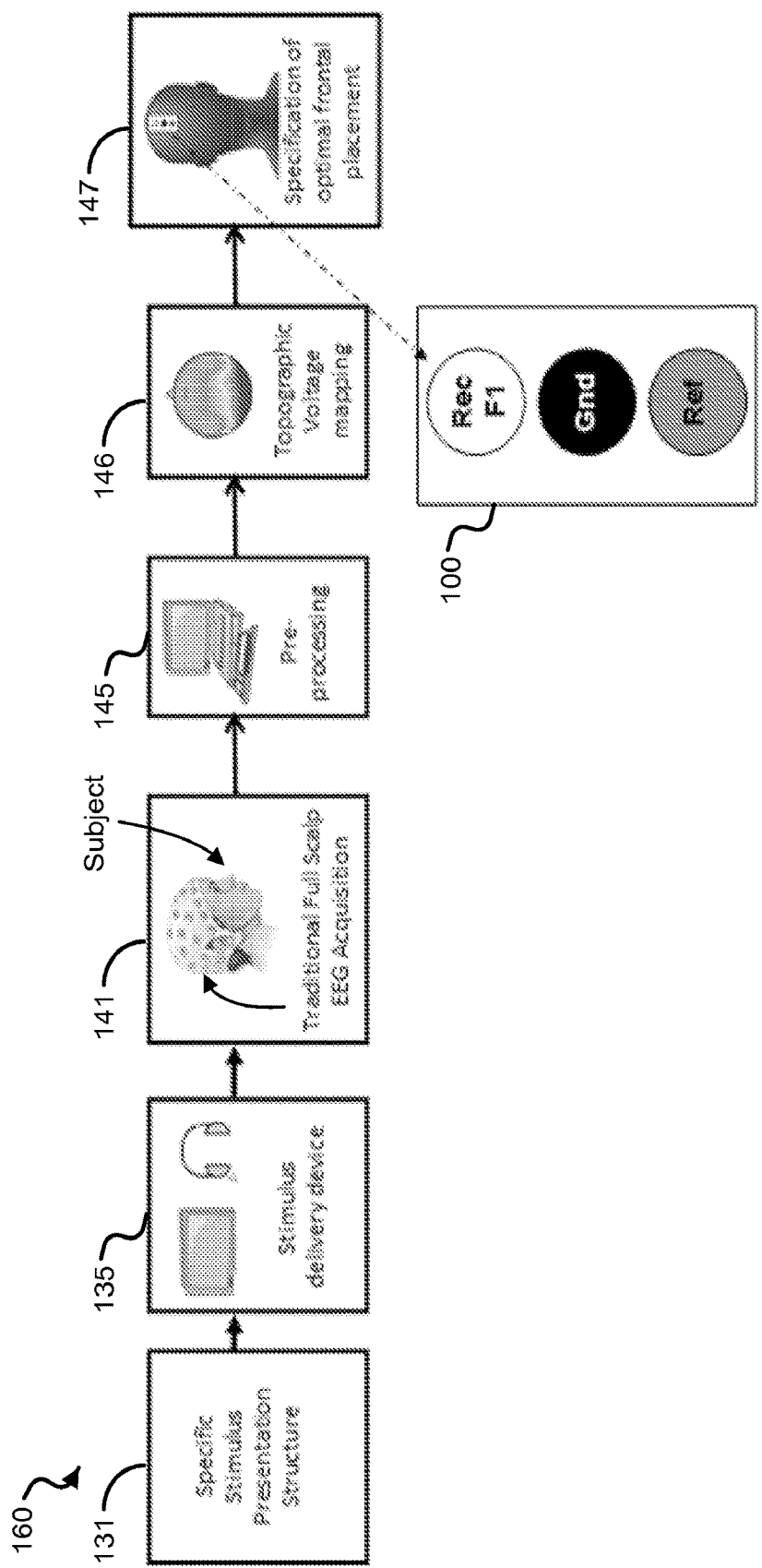
FIG. 1G shows a diagram of an exemplary method to determine an electrode configuration on the frontal region of a subject's head.

FIG. 1G shows an illustrative diagram depicting an exemplary method 160 to determine optimal spatial placement of frontal electrode sensors to acquire EEG event-related potentials. The method 160 includes presenting the stimulus presentation structure 131 using the stimulus delivery module 135 to a subject, who can wear a conventional 'full scalp'

EEG acquisition device with electrodes located at positions across the subject's head. The stimulus presentation structure 131 can be used to effectuate a presentation of a stimulus or a sequence of stimuli to a subject. The EEG response of the subject to the presentation of the stimulus or sequence of stimuli is acquired using the 'full scalp' EEG acquisition device to acquire the EEG signal data from a plurality of electrodes across a plurality of regions of the brain, e.g., including frontal, parietal, occipital, and temporal cerebral regions. The acquired data can be analyzed using the pre-processing module 145 to implement pre-processing analysis techniques on the acquired data. In some examples, the pre-processing analysis techniques include producing one or more topographical voltage maps 146 of the electrophysiological data, e.g., which can be over different temporal and/or spatial parameters. For example, the pre-processing module 145 can utilize the data produced in the topographical voltage map(s) 146 in data processing techniques to optimize spatial arrangement parameters of the electrodes that can be included in a frontal electrode physiological sensor device. For example, the spatial arrangement parameters can include the number of electrodes, electrode type and size, location/placement of each electrode, spacing between the electrodes, etc. For example, determination of the location and/or placement of the electrodes can be based on the type of signal to be recorded (e.g., signal of interest, a reference signal, and ground signal). For example, the electrode location and/or placement parameters can include relative distances of the electrodes, particular placements of the electrodes with respect to the subject's frontal region of his/her head, etc. For example, such parameters (e.g., type, quantity, size, placement, relative position, etc.) of the electrodes configured in exemplary physiological sensor devices of the disclosed technology account for topography, amplitude, and localization of physiological signals of interest (e.g., including event-related potential brain markers), as well as specific metal conductance, resistance, and spacing parameters.

Exemplary Implementations of the Disclosed Devices with Methods and Systems for Profiling Cognitive-Sensory Function Described are exemplary implementations of the disclosed frontal electrode physiological sensor devices and systems and methods using such devices for providing a cognitive and/or sensory assessment of a subject (or a group) indicative of one or more aspects of cognitive or sensory functions. The described exemplary implementations include eliciting and extracting various brain ERPs (e.g., P300, notion/feeling of 'reward', and mismatch negativity) measured by EEG recordings using visual stimuli and auditory stimuli to produce an information set providing quantitative values corresponding to the cognitive performance, sensory performance, and/or awareness state profile. In some examples of the disclosed methods and systems, eye tracking data can be used in addition to the exemplary EEG recording physiological data acquired by the exemplary frontal electrode physiological sensor devices for providing the cognitive and/or sensory assessment.

In the described examples, specific stimuli sets are presented while recording EEG signals from the subject to elicit event-related potentials of interest, as well as correlated neural frequency oscillations. The exemplary ERPs used in the exemplary implementations include, but are not limited to, the P300, notion/feeling of 'reward', and the mismatch negativity. Other exemplary ERPs that can be implemented to provide an exemplary cognitive-sensory profile using the disclosed technology can include the N400, among others.

As described below, exemplary applications of the exemplary frontal electrode physiological sensor devices with the disclosed methods and systems use the exemplary P300, 'reward', and mismatch negativity ERPs as illustrative examples to described how the exemplary methods can be implemented, e.g., stimuli design and presentation, physiological signal (e.g., EEG) recording, physiological data (e.g., ERP) analysis, and cognitive and/or sensory profile generation (e.g., including inferred cognitive and/or awareness states).

The disclosed cognitive and/or sensory profile generation methods and systems can be used to measure brain markers, but in addition, it evaluates and transforms this information into a new type of purposeful data that creates an individual knowledge evaluation and/or state of awareness profile. Moreover, in some implementations, for example, the disclosed methods and systems can use this profile to guide a brain-machine interface system.

I. P300 and "Reward"

The P300 is a brain endogenous response characterized by a positive-going electrical response between 300 and 800 ms, with a central-parietal maxima scalp distribution. The P300 is inversely correlated with an item's subjective probability of occurrence. For example, the P300 has been used in visual target detection tasks, where the target elicits higher amplitude P300s than the other items.

Additionally, in the exemplary implementations described herein using the P300, an arbitrary visual cue (e.g., green circle) was created, and the tested subjects were instructed to associate it with a notion or feeling of "reward". For example, the subjects were instructed to associate the exemplary green circle with a cue of good task performance and informed that the occurrence of the cue during testing would be correlated with increase compensation after the test, thus, creating an association of this arbitrary cue with a notion of "reward". The brain responses to this "reward" stimulus was subsequently analyzed. The exemplary illustrations of the disclosed methods using P300 illustrates the broad applicability of the methods across various EEG recording techniques. For example, the method can be applied to assess cognitive and/or sensory profiles using brain data (e.g., EEG signals) recorded using a traditional rigid electrodes EEG system with the disclosed frontal electrode configurations, as well as with EEG data acquired using wearable, flexible epidermal electronic sensors with the disclosed frontal electrode configurations.

I.1. Exemplary Stimulus Presentation Structure

In some exemplary implementations of the P300 and "reward" ERPs, visual stimulation were used. For example, the stimuli were comprised of multiple image categories, e.g., including animals; cars; faces; flowers; houses; random objects; motorcycles; airplanes; and buildings. The exemplary pool of stimuli was obtained from various resources.

Figure 2:
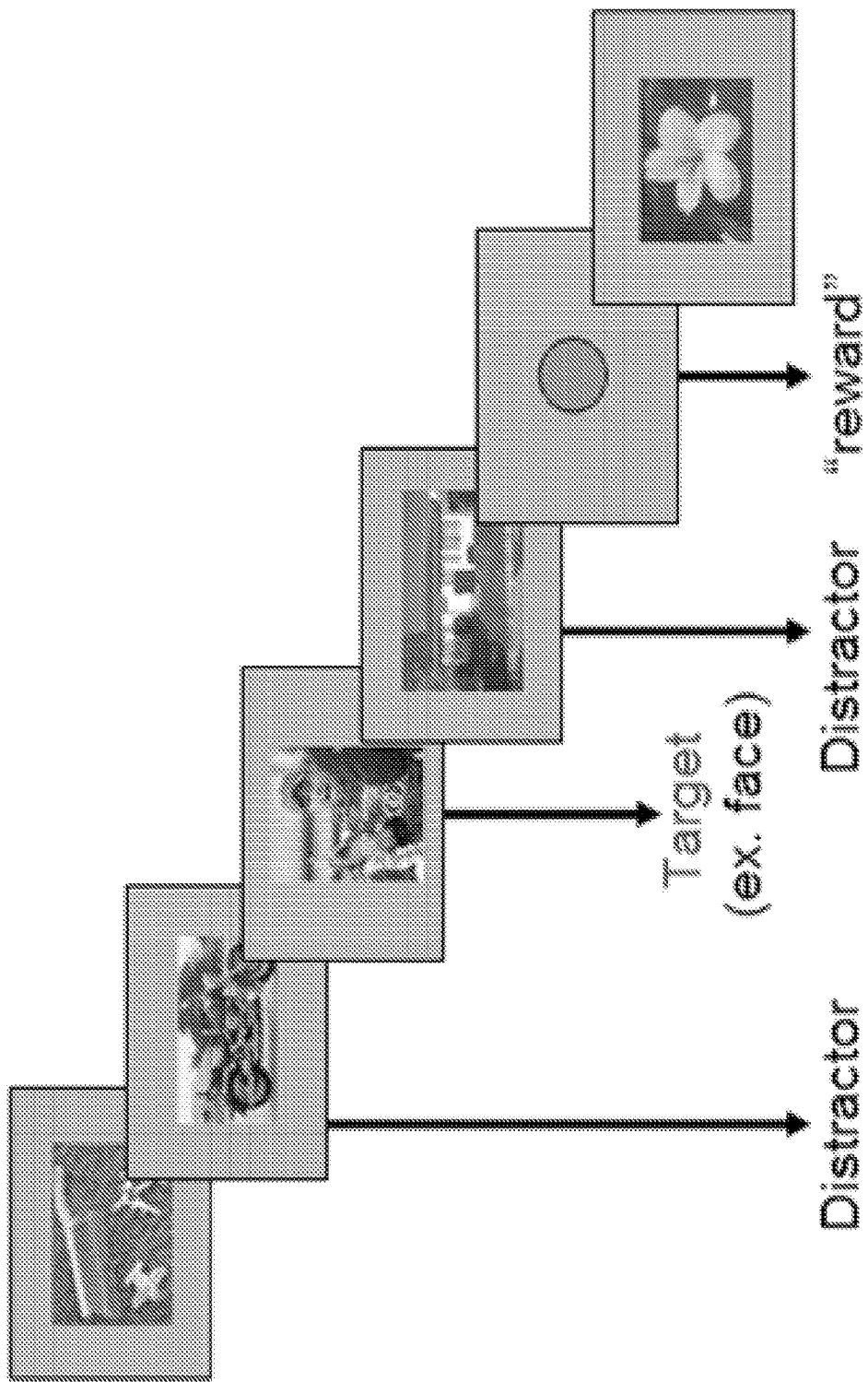
FIG. 2 shows a diagram of an exemplary sequence of presented visual stimuli.

FIG. 2 shows a diagram of an exemplary sequence of presented visual stimuli. This diagram portrays images of specific presented exemplars and the pre-programmed pseudo-randomized order of presentation Having the adequate stimuli presentation structure for each solution is an intrinsic and important part of the exemplary method. In this example, the relevant aspect is the distinction between the images that represent pre-determined "Targets" versus all other images (labeled as "Distractors") and versus the green circle previously associated with an indication of "Reward". The adequate stimuli structure (e.g., in this case, the specific content of images of interest as targets embedded in a sequence of other images, location of presentation, timing of presentation, timing of inter-stimulus interval, etc.) and the described specialized subsequent analysis are important in the exemplary method to how to use relevant brain markers, e.g., in this exemplary case, the P300 and the "reward" elicited ERPs, to evaluate and determine individual knowledge, levels of attention and preferences to specific items.

I.2. Exemplary Stimulus Delivery Device

The exemplary pool of stimuli was obtained from various resources. After obtaining the stimuli pool, each exemplar's relative luminance was controlled using a computer implemented method (e.g., programmed with a MATLAB script). For example, the computer implemented method was implemented to first load in a color image, and calculate its relative luminance using the following exemplary formula, where Y, R, G, and B represent relative luminance, red gun values, green gun values, and blue gun values, respectively:

$$Y=0.2126R+0.7152G+0.0722B \tag{1}$$

For example, the desired relative luminance was set to be a value equal to 120. After the script measured the initial relative luminance of each image, it either added or subtracted RGB values to every pixel within the image in order to achieve an average relative luminance of 120. Images were then saved at 100% quality.

After controlling for luminance, another computer implemented process (e.g., programmed using a MATLAB script) was used to place a centrally positioned fixation dot on each stimulus exemplar. For example, this helped the subject to maintain fixation and minimize any frequent eye saccades. This exemplary process first measured the dimensions of an uploaded image. It used these measurements to calculate the center of the image and subsequently create a fixation dot using the standard equation of a circle. Pixels within a seven pixels length radius around the center were altered by changing the pixels' red gun to 255, the green gun to 0, and the blue gun to 0.

Lastly, the visual stimuli for the fixation dot and an arbitrary visual cue for "reward" were created. For example, for the fixation dot, a computer implemented process (e.g., programmed using a MATLAB script) was used to create a grey background image (e.g., red gun equal to 150; green gun equal to 150; blue gun equal to 150) with a height and width of 350 pixels. Then, the exemplary script ran a nested for-loop using the standard equation of a circle to alter pixels within a seven pixels length radius to red, e.g., by changing the image's red gun to 255, the green gun to 0, and the blue gun to 0. For the "reward", imaging software was used to create a green circle (e.g., red gun equal to 0; green gun equal to 255; blue gun equal to 0) on a 350×350 pixels grey background (e.g., red gun equal to 150; green gun equal to 150; blue gun equal to 150) background.

The exemplary stimulus presentation paradigm that was used in this example stimuli presentation process was programmed using Cogent 2000, and included presenting visual stimuli serially with brief presentation durations. For example, the pool of stimuli, not including the fixation dot and green circle, was divided into two groups, one for each of the two recording techniques. Each technique included 900 stimuli, for a total of 1800 stimuli across recording techniques. For example, within a technique, the 900 stimuli, including targets and distractors, each presented for 100 ms, were divided into three presentation blocks. The green circle stimulus presentation lasted 1000 ms and was shown 30 times within each presentation block. The fixation dot was visible during every target trial, distractor trial, and inter-stimulus interval (ISI).

For example, in block 1, targets were human faces. In block 2, targets were cars. In block 3, targets were animals. In addition to randomizing the order of the recording techniques, for example, the order of the presentation blocks within each technique was also randomized Presentation blocks were never repeated consecutively (e.g., block 1, block 2, block 3, block 3, block 2, block 1, block 1, block 3, block 2) across techniques. Because the subject was instructed to count how many times he/she saw a particular target, the correct number of targets was varied for each block. For example, in block 1 (target: faces), there were 56 targets and 244 distractors. For example, in block 2 (target: cars), there were 62 targets and 238 distractors. For example, in block 3 (target: animals), there were 60 targets and 240 distractors. Distractors were composed of all of the non-target object categories. For example, in block 1 (target: faces), the distractors included cars, animals, flowers, houses, etc. The exemplary MATLAB code began by prompting the experimenter to enter the subject's initials and choose which block to present. Depending on the chosen block number, the script calculated which object category would be target, the number of targets, and the number of distractors. Afterward, it randomized the order of stimulus presentation using the MATLAB randperm( ) function. It ran the randperm( ) function twenty times to better randomize the presentation sequence. Then, it created inter-stimulus intervals (ISI) for each trial using the randi( ) function. The inter-stimulus intervals ranged from 500 ms to 600 ms. In addition to configuring the display, sound card, and parallel port, a log file was configured and initialized within Cogent 2000. This log file was used to create a history of every trial regarding its stimulus type (e.g., target, distractor and green circle). Subsequently, the stimuli were loaded into memory buffers. The aforementioned steps were executed prior to stimulus presentation, e.g., to reduce computational load and increase latency precision. The stimulus presentation included a for-loop that iterated down the pre-determined presentation order. For example, based on the value of the current stimulus in the presentation order, the computer implemented process calculated its stimulus type and sent the appropriate information regarding its stimulus type to the log file and parallel port, whose trigger was sent to the EEG recording computer. Then, the program presented the ISI. At the end of each presentation, the parallel port was reset to zero to prepare for the next trial.

I.3. Exemplary EEG Recordings Using Traditional Full Scalp EEG Acquisition

To prepare the exemplary subjects for EEG recording, each subject was seated in a chair in a recording chamber to begin an EEG capping process. For the exemplary implementations using the rigid electrode modality (e.g., Brain Products), this process involved placing a traditional EEG cap on the subject's head and securing it with an elastic chin strap. In some examples, either a 56 cm or a 58 cm diameter cap was used, e.g., based on the estimated size of the subject's head. Next, Signa electrode gel (e.g., from Parker Laboratories) was injected using a curved, plastic syringe under each of the cap's electrodes to create a conductive bridge between the electrode itself and the subject's scalp. Also, for example, wooden Q-tips were used to massage the gel in order to build a stronger conductance by lowering the impedance. For example, use of this technique lowered the impedance levels to <5 kΩ for each electrode, e.g., including the ground and reference.

Before starting the exemplary implementation using EEG recordings, subjects were given an instructions document to read. For example, this document described the general organization of the experimental paradigm and what they would be viewing, namely targets, distractors, a fixation dot and a green circle. It was also explained that in each presentation block, the target would change. For example, in block 1, the task was to count how many times they saw an image with one or more human faces. In block 2, the task was to count how many times they saw an image with one or more cars. In block 3, the task was to count how many times they saw an image with one or more animals. The subjects were instructed to regard all other photographs as distractors and not count them. After each presentation block, the subjects were asked to report how many targets they saw. For example, the green circle indicated reward. The subjects were seated in front of the presentation monitor and asked to just maintain visual fixation on a red, central fixation dot throughout the duration of the experiment and restrict their motor movements as much as possible to prevent motion artifacts in the neurophysiological data. Afterwards, the recording room's lights were then dimmed, and the stimulation process and EEG recordings began.

In these exemplary implementations, a traditional EEG system with rigid electrodes was used to acquire brain waves. The exemplary EEG system included a BrainAmp DC 32-channel system; BrainVision Recorder; Fast n Easy 32-channel EEG recording cap size 56 cm; Fast n Easy 32-channel EEG recording cap size 58 cm; PCB Ribbon Cable for BrainCap-MR with 5 k resistors; and BrainCap MR Box 1.2.

I.4. Exemplary EEG Analytical Processing and ERP Analysis

Data analysis techniques included multiple steps and processes, e.g., including the processing of marker data and individual statistical analysis.

Processing of marker data: For example, after each recording session, the exemplary EEG recordings system produced three files: data file (.eeg), header file (.vhdr), and marker file (.vmrk). The marker files contained the event triggers for each stimulus onset. In this example, because of output limitations within the parallel port, the Cogent 2000 log file was used to hold more readable information regarding an exemplar's stimulus type (e.g., target, distractor, or green circle). From there, a process (e.g., programmed using a MATLAB script) was used to replace the event triggers in the marker file (.vmrk) with the event codes from the log file in a one-to-one replacement. For example, the first marker in the .vmrk file was replaced by the first marker in the log file; the second marker in the .vmrk file was replaced by the second marker in the log file, etc.

Exemplary individual statistical analysis: Using the abovementioned exemplary markers for onset of stimulus presentation, an ERP analysis was performed following exemplary analytical methods to calculate ERPs (e.g., using BrainVision Analyzer 2). For example, ERP waveforms were calculated for "Targets", "Distractors" and "Reward". Subsequently, for example, from each ERP waveform the spatial location and timing of the ERP components of interest were determined. For example, for each time-window of interest, topographic voltage maps for each ERP component of interest were calculated using the available voltage information from every electrode in the EEG cap (total 32 electrodes). In the exemplary implementations described herein, a combination of MATLAB and Statsoft Statistica (version 8.0) software was used for statistical analyses.

I.5. Exemplary Configuration of Optimal Frontal Electrode Placement

The determination of an optimal electrode placement using our method can be obtained by integrating all this information, for example: (i.) Sensory or cognitive neuropsychological mechanism of interest; (ii.) Designing an adequate stimulus presentation and delivery method for eliciting the neuropsychological mechanism of interest; (iii.) Tag chronological markers associated with onset of stimulus presentation; (iv.) Record EEG signals from the subject during stimulation; (v.) Analyze EEG data and calculate ERPs for each condition/marker of interest; (vi.) Identify ERP components of interest in every channel of the dataset; (vii.) For each component of interest, determine latency (time of occurrence) and spatial distribution (which electrodes show the ERP of interest); (viii.) Based on the latency of each component of interest, determine a time-window of occurrence for each component and create topographic voltage maps; (ix.) For each ERP component of interest, investigate where in the scalp it has a significant "expression" (i.e., in which electrodes is it present and how is its voltage distributed in the topographic voltage map); (x.) Use this information to determine the best timing and the optimal location for electrodes placement to detect modulations of the ERP of interest, as well as its expression in frontal electrodes. For example, from this, a determination of an optimal placement and configuration of electrodes for detection of an ERP of interest can be made.

In the exemplary frontal electrode configuration, using the disclosed electrode configuration optimization method, spatial locations and placement (e.g., including distance between electrodes and electrode sizes) were determined in a way to minimize the used forehead "real estate" occupied, while keeping enough spacing to respect each electrode signal integrity along the scalp surface and detect the brain activity of interest. Typically, for example, the reference electrode is positioned away from the recording electrode and in a location where the "brain function of interest" is minimal or provides no expression. In this way, when one is differentiating the reference signal from the recording signal, it wouldn't be 'subtracting' anything of interest. However, large separations use relatively large amounts of spatial area on the forehead. In devices of the disclosed technology, a minimal configuration of electrodes are placed on the frontal region of the subject that require the minimal amount of spatial area (e.g., placing the recording and reference electrodes close together) while still providing reliable physiological signal readings and detection. The disclosed electrode configuration optimization method was implemented to obtain such configurations.

For example, assuming additive white Gaussian noise in the sensor, the accuracy of an optimal classifier (e.g., given by a likelihood ratio test) is a monotonic function of the energy in the difference between the scalp potential of the recording electrode under the null hypothesis (for example the "Distractors" in the P300 paradigm) and scalp potential of the recording electrode under the alternate hypothesis (for example the "Targets" in the P300 paradigm). Thus, provided is a criterion for maximizing classification accuracy which is equivalent to maximizing the energy in the difference between the recording electrode's potential in "Targets" and "Distractors" setting.

If an electrode pair is placed across isopotential lines (e.g., same or identical voltage potential values), then the potential difference is sensitive to current flow from regions of high to low, or low to high, potentials. This is referred to as placing the electrode pair along a gradient potential. However, if the bipolar pair is placed along an isopotential line, then a zero, or close to zero differential potential is recorded.

Maximizing energy in the difference is done when the placement of the frontal electrodes is along the gradient of the frontal scalp distribution of the brain signal of interest.

From the exemplary analysis in both ERPs used in the exemplary implementations, e.g., P300 and "reward", the gradients of the voltage scalp distribution are oriented vertically. For better detection of these ERPs, the recording electrode, ground electrode and reference electrode should be placed from top to bottom (e.g., from the top of the forehead towards the nose), which is across the isopotential line. Moreover, placing the recording electrode, ground electrode, and reference electrode orthogonal to that direction (e.g., along the isopotential line) will result in a degraded classification performance—approaching that of chance.

Moreover, for example, in addition to increasing signal-to-noise characteristics in the detected electrophysiological signals, the disclosed top-to-bottom (e.g., top of the forehead towards the nose) frontal region electrode configuration also is capable of detecting relevant neurophysiological signals of the underlying functional-neuroanatomy (e.g., the human brain has symmetrical hemispheres along a mid-sagittal line and that many sensory and cognitive processes occur with functional and anatomical hemispheric asymmetries). For example, placing the electrodes along the brain axial (or transversal) plane (e.g., along the forehead from left to right), instead of the disclosed top of the forehead towards the nose orientation, is likely to create significant vulnerabilities to brain hemispheric artifacts leading to erroneous EEG/ERP readings. Also, the exemplary methodology of the disclosed technology also suggests that the greater the expression of an event-related potential is in frontal voltage scalp distributions, the easier it is to classify.

Figure 3A:
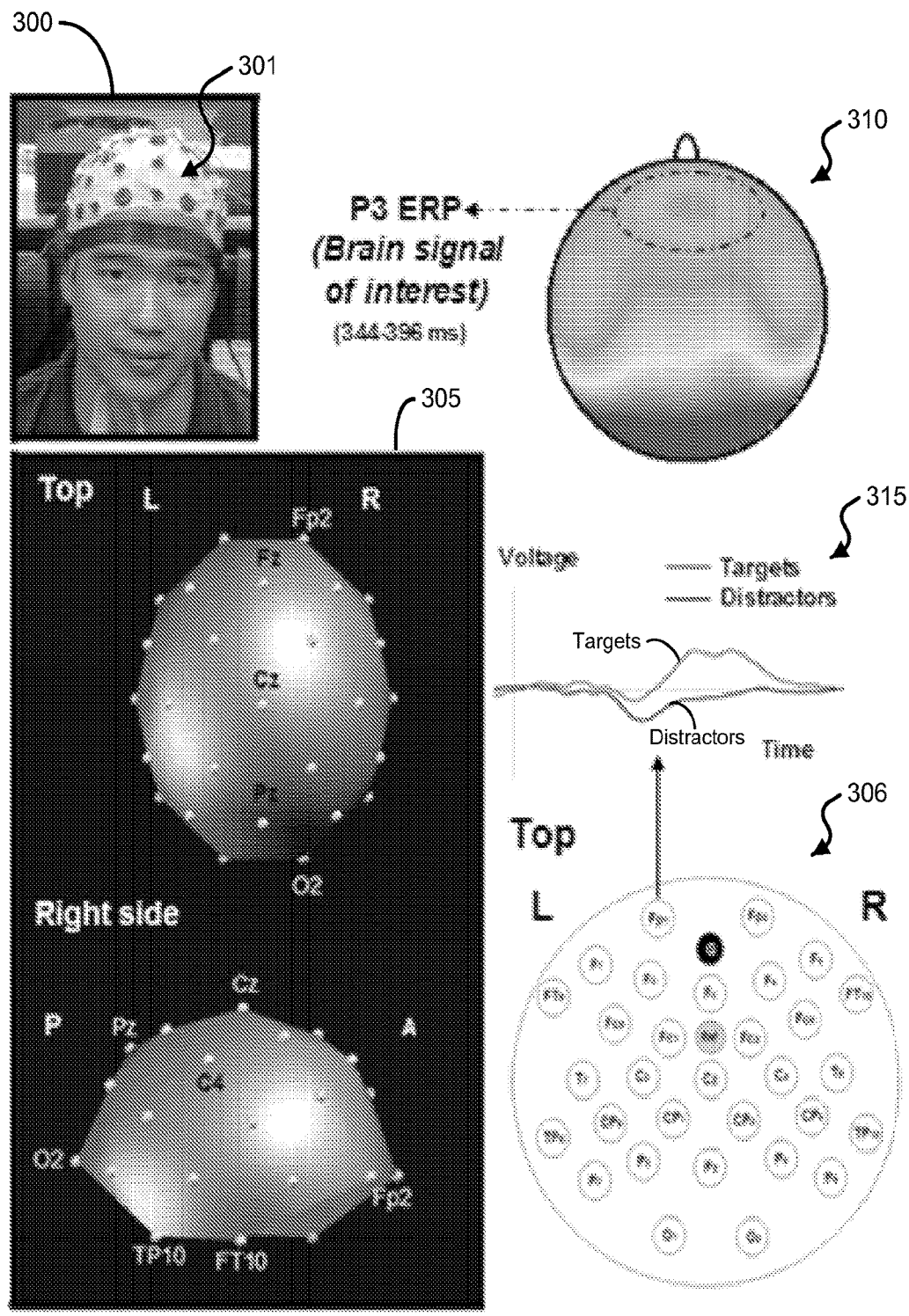
FIG. 3A shows diagrams illustrating an exemplary frontal electrode configuration using a conventional EEG system and exemplary results from its implementation for detecting the EEG signal responses.

FIG. 3A shows diagrams illustrating an exemplary frontal electrode configuration using a conventional EEG system and exemplary results from its implementation for detecting the EEG signal response to P300 ERP detection of "Targets" and "Distractors". In FIG. 3A, an image 300 is shown of an exemplary subject wearing a conventional EEG rigid electrode detection cap 301. In FIG. 3A, a diagram 305 is shown depicting a tridimensional reconstruction and top and right side schematical views of the 32 electrodes' location in the conventional EEG rigid electrode detection cap 301. In FIG. 3A, a diagram 306 is shown depicting a two dimensional views of the 32 electrodes' location in the conventional EEG rigid electrode detection cap 301. As shown in FIG. 3A, a diagram 310 shows an exemplary topographic voltage map (e.g., with indication of the frontal expression of ERP of interest, in this exemplary case, a P300 ERP for "Targets" in an exemplary analyzed time-window (e.g., 344-396 ms). As shown in FIG. 3A, a data plot 315 shows the exemplary ERP waveforms from a frontal electrode (Fp1) for both "Targets" (—red line) and "Distractors" (—black line). As shown in the topographic voltage map 310, a hemispherically symmetric distribution is present, where isopotential lines are on the transversal plane. As such, the frontal electrodes are placed orthogonal to the transversal plane, across the isopotential line.

Figure 3B:
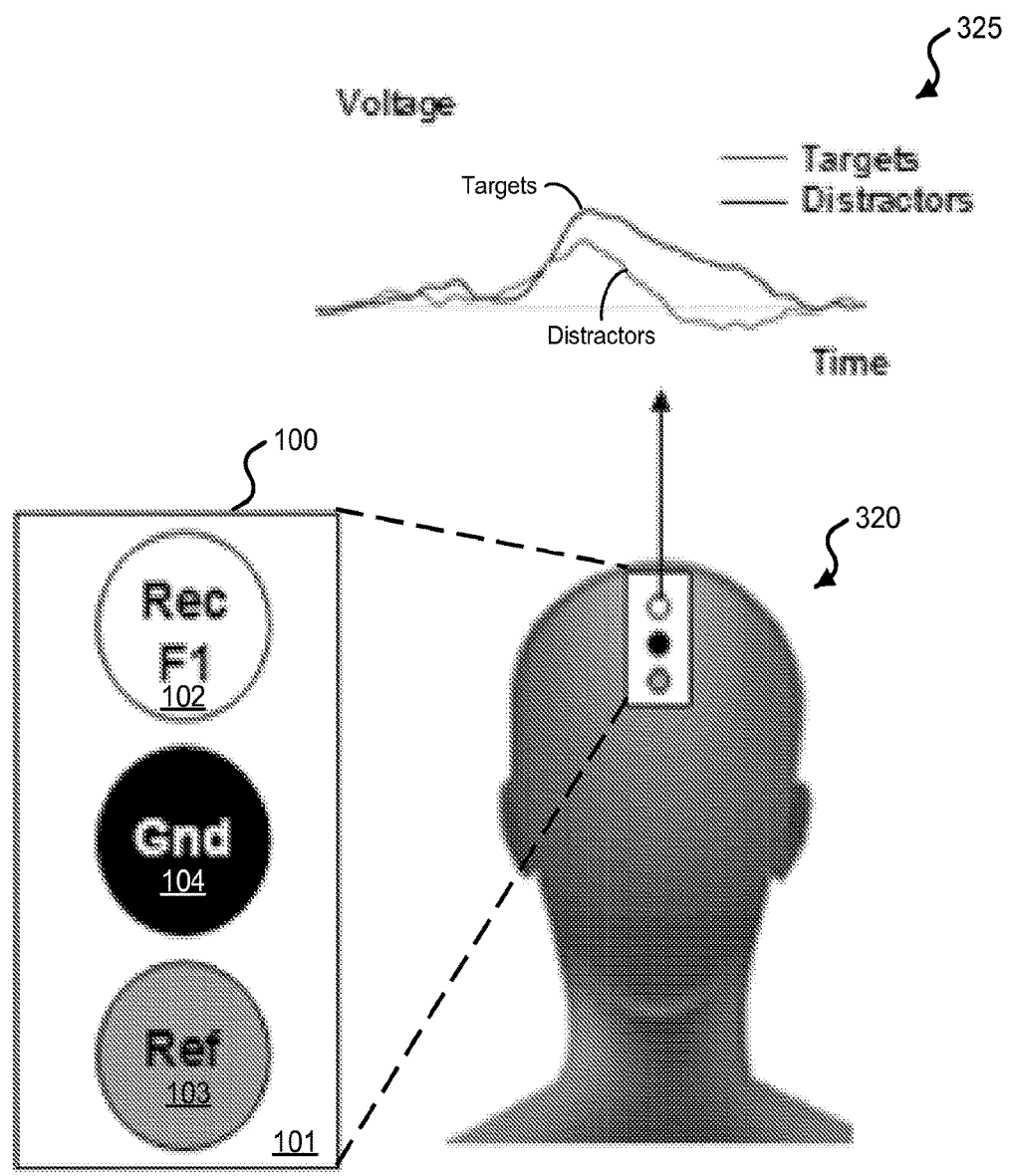
FIG. 3B shows diagrams illustrating an exemplary frontal electrode configuration using an exemplary three-electrode sensor device and exemplary results from its implementation for detecting the EEG signal responses.

FIG. 3B shows diagrams illustrating an exemplary frontal electrode configuration using an exemplary three-electrode frontal sensor device and exemplary results from its implementation for detecting the EEG signal response to P300 ERP detection of "Targets" and "Distractors". FIG. 3B shows a diagram 320 of the frontal electrode sensor device 100 in physical contact with the frontal region of a subject's head and aligned across an isopotential line (e.g., with the recording electrode placed toward the top of the forehead, the reference electrode placed toward the nose on the forehead, and the ground electrode placed between the recording and reference electrodes). FIG. 3B shows a data plot 325 of the ERP waveforms acquired from the frontal recording electrode (e.g., Rec F1—white circle 102) for both "Targets"—red line and "Distractors"—black line. The disclosed frontal electrode configuration in the 3-electrode sensor devices can detect the ERPs of interest ("Targets" and "Distractors") as reliably as a full cap traditional EEG system. In this example, the polarity of the ERPs ("Targets" and "Distractors") is reversed between the exemplary frontal system and the EEG cap frontal electrode due to the relative position of the "Reference" electrode in regards to the "Recording" electrode. For example, in the full cap system shown in FIG. 3A, the "Recording" electrode occupies a significantly more anterior position than the "Reference", while in the exemplary system shown in FIG. 3B, the "Reference" electrode is in a lower and slightly more anterior position than the "Recording" electrode.

I.6. Exemplary Implementations of Frontal Electrode Configurations for ERP Detection Across Different Technologies In these exemplary implementations, the disclosed frontal electrode configurations were implemented across different electrode types and materials, e.g., including EEG recording technologies using a traditional full EEG cap with rigid electrodes and three classes of frontal electrode sensor technologies containing a ground, reference, and recording electrode, using: (1) exemplary rigid sensors (e.g., obtained from Brain Products); (2) exemplary custom-designed rigid sensors; and (3) an exemplary epidermal electronics sensor device with flexible electronics electrodes.

For example, after subject preparation, stimulus presentation, EEG recordings and processing of marker files, as described in the previous sections, a combination of MATLAB and Statsoft Statistica (version 8.0) software were used for statistical analyses. For example, after data processing and analysis, BrainVision Analyzer exported text files containing data values in regards to condition, subject, trial, electrode channel, and mean voltage amplitude. For each recording technology, the mean voltage amplitude was extracted from a frontal electrode for the following time intervals of interest, for example: Targets and Distractors, 400 ms to 500 ms after stimulus onset; Reward stimuli, 456 ms to 556 ms after stimulus onset. The same exemplary parameters were used in all the exemplary techniques (e.g., the exemplary rigid electrodes from Brain Products, the exemplary custom-designed rigid electrodes, and the exemplary EES flexible electrode sensors). For example, these data were written to text files by BrainVision Analyzer and subsequently loaded into an exemplary MATLAB program that we created to sort and organize the data in a more accessible format. Specifically, for example, the exemplary script allowed an easier data selection process by column, e.g., using MATLAB's variable editor. After selecting, data were put into Statistica data spreadsheets. In some examples, one-way (factor 1: condition) repeated measures ANOVAs were performed on each Statistica spreadsheet for the comparison between distractors and targets for each of the EEG recording techniques. For example, each spreadsheet was specific to the following: 1) EEG technology; and 2) comparison: distractors vs. targets. For the reward condition, for example, a T-test was performed comparing the reward's extracted mean amplitude values against zero. For the rewards condition, for example, each spreadsheet was specific to the following: 1) EEG technology; and 2) comparison: reward vs. zero.

I.6.1. Using Rigid EEG Sensors in Frontal Configurations

Figures 4A, 4B:
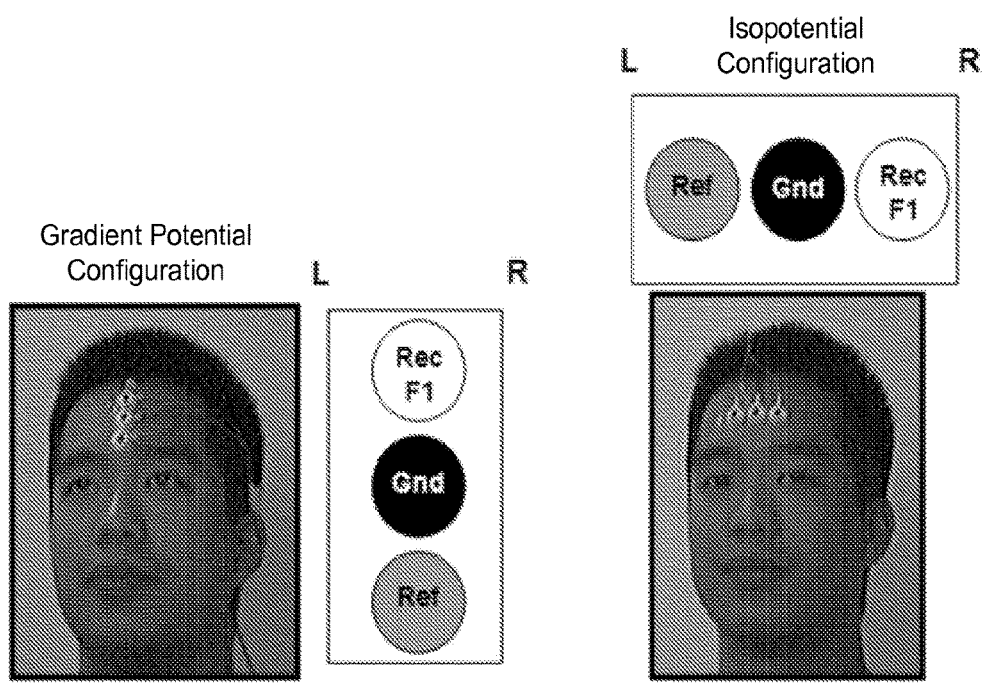
FIGS. 4A and 4B show exemplary three-electrode configurations using exemplary rigid electrodes along a gradient potential configuration and along an isopotential configuration, respectively.

Two frontal configurations including a horizontal anatomical alignment of the electrodes along the transverse direction (e.g., left to right axis) and a vertical anatomical alignment of the electrodes along the sagittal direction (e.g., posterior-anterior axis) were implemented using exemplary rigid EEG electrodes (Brain Products). FIGS. 4A and 4B show exemplary three-electrode configurations using rigid electrodes along a gradient potential configuration and along an isopotential configuration, respectively. In one example, a gradient potential configuration (referred to here as "vertical-sagittal") used three electrodes placed from the top of the forehead towards the nose, as follows: "Recording F1" electrode, "Ground" electrode, "Reference" electrode, as shown in FIG. 4A. In another example, an isopotential configuration (referred here as "horizontal-transverse") used three electrodes placed along the forehead from left to right, as follows: "Reference" electrode, "Ground" electrode, "Recording F1" electrode, as shown in FIG. 4B.

FIG. 5 shows data plots of an exemplary EEG online recording acquired using the exemplary rigid electrodes (e.g., obtained from Brain Products) before stimuli presentation for both gradient potential and isopotential configurations. The data plot 510 shows the exemplary EEG data for the isopotential configuration of the exemplary three-electrode frontal rigid EEG sensor. The data plot 520 shows the exemplary EEG data for the gradient potential configuration of the exemplary three-electrode frontal rigid EEG sensor. Eye blinks were used to better illustrate the signal-to-noise (SNR) ratio of the response in this example.

Figure 6:
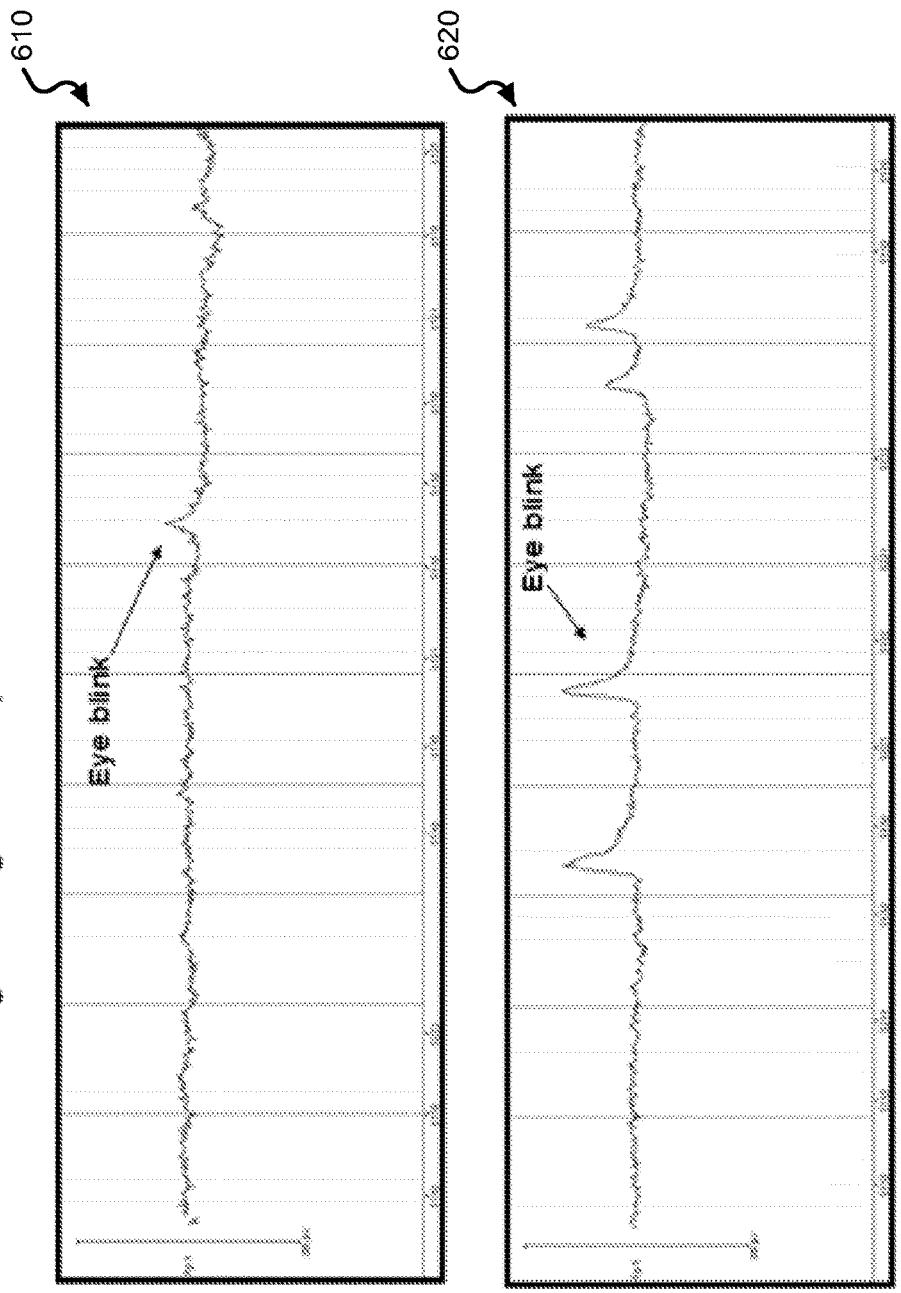
FIG. 6 shows data plots of an exemplary EEG online recording using the exemplary rigid electrodes during an exemplary stimuli presentation for both gradient potential and isopotential configurations.

FIG. 6 shows data plots of an exemplary EEG online recording acquired using the exemplary rigid electrodes during an exemplary stimuli presentation for both gradient potential and isopotential configurations. The data plot 610 shows the exemplary EEG response data for the isopotential configuration of the exemplary three-electrode frontal rigid EEG sensor. The data plot 620 shows the exemplary EEG response data for the gradient potential configuration of the exemplary three-electrode frontal rigid EEG sensor. Eye blinks were used to better illustrate the signal-to-noise (SNR) ratio of the response in this example.

As shown in FIGS. 5 and 6, it is noted that in both cases the eye blinks are more pronounced in the gradient potential directions as compared to the isopotential ones, e.g., indicating a better performance, as predicted, for the "vertical-sagittal" configuration.

Figure 7A:
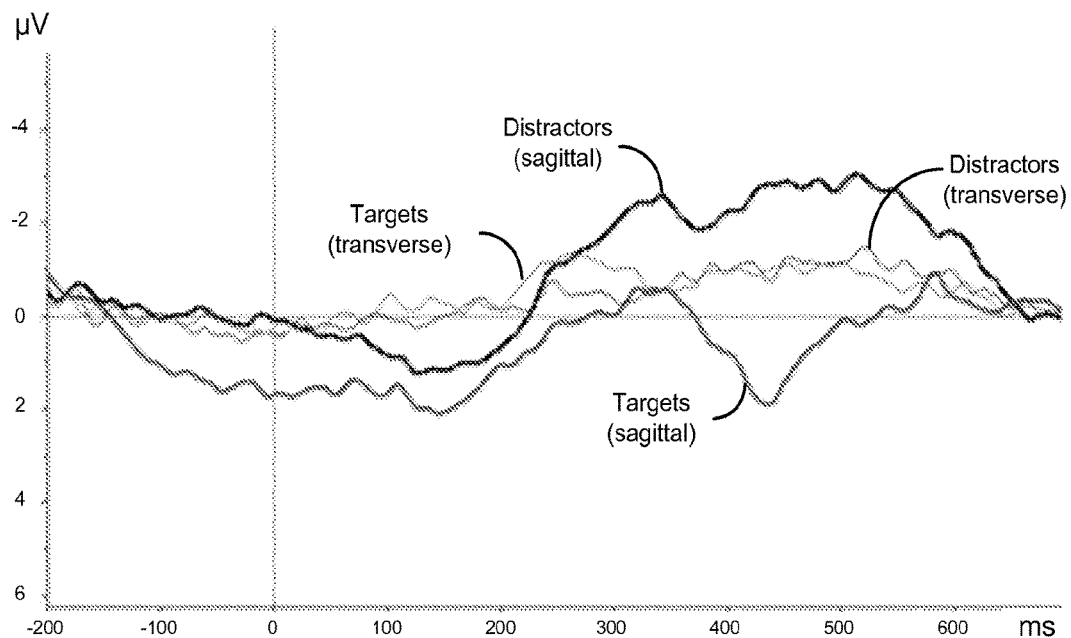
FIG. 7A shows an exemplary data plot of ERP waveforms from a single subject for "Targets" and "Distractors" using the exemplary rigid electrodes.

FIG. 7A shows an exemplary data plot of ERP waveforms acquired using the exemplary rigid electrodes from a single subject for "Targets" (red line) and "Distractors" (black line) using both the "vertical-sagittal" configuration (gradient potential configuration, shown by thicker lines) and the "horizontal-transverse" configuration (isopotential configuration, shown by thinner lines).

Figure 7B:
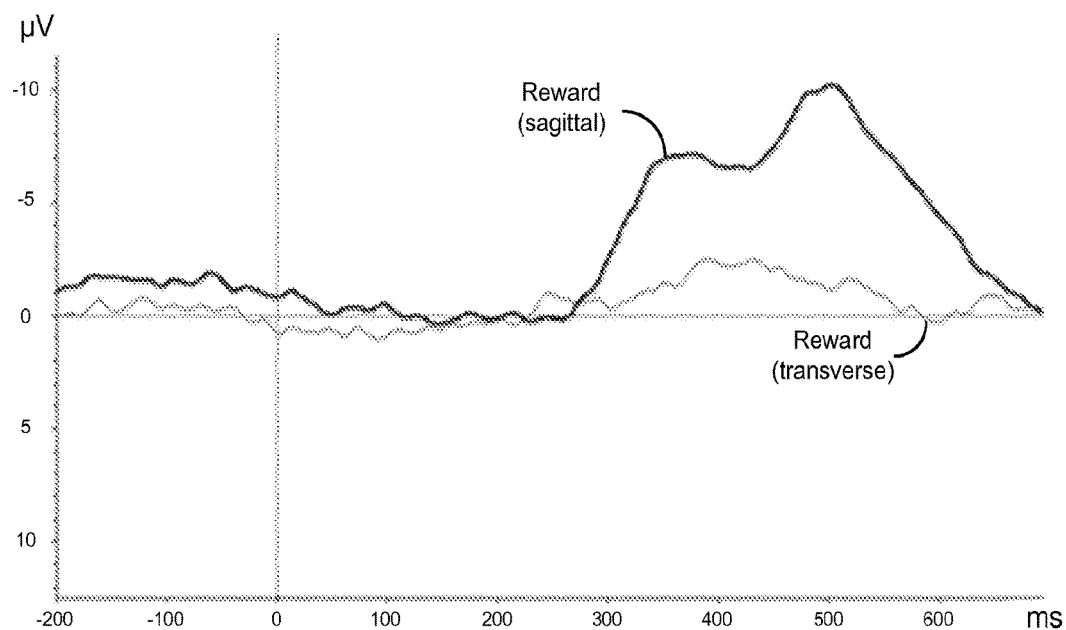
FIG. 7B shows an exemplary data plot of ERP waveforms from a single subject for "Reward" using the exemplary rigid electrodes.

FIG. 7B shows an exemplary data plot of ERP waveforms acquired using the exemplary rigid electrodes from a single subject for "Reward" (blue line) using both the "vertical-sagittal" configuration (gradient potential configuration, shown by thicker lines) and the "horizontal-transverse" configuration (isopotential configuration, shown by thinner lines).

The exemplary results of the exemplary implementations using the exemplary rigid electrode sensors showed adequate detection for all tested ERPs across the isopotential line in the gradient potential configuration, e.g., Targets vs. Distractors N=132, F=5.100, p<0.05; and Reward N=45, T=−3.03, p<0.005. Conversely, the exemplary results of the exemplary implementations using the exemplary rigid electrode sensors showed inadequate detection for all tested ERPs along the isopotential configuration, e.g., Targets vs. Distractors N=144, F=0.001, p=0.96; and Reward N=45, T=−1.45, p=0.15. The disclosed three-electrode frontal configuration using the gradient potential configuration is capable of efficient ERP detection using rigid electrodes.

I.6.2. Using Custom-designed Rigid EEG Sensors in the Gradient Potential Configuration Different rigid electrode sensors using the disclosed optimal three-electrode frontal configuration were compared in the following exemplary implementations. For example, the customized-designed rigid electrode sensors were fabricated.

For example, rigid forehead sensors were fabricated using an exemplary micro-fabrication method involving gold, polyimide, and Tegaderm. The exemplary micro-fabrication method included a first process to deposit Au (e.g., 200 nm) onto adhesive polyimide tape by E-beam evaporation or sputtering. The exemplary micro-fabrication method included a second process to cut polyimide tape into small rectangle, e.g., with aspect ratio of 1:3. The 3 square portions are called left, middle, and right, with adhesive side facing up. The exemplary micro-fabrication method included a third process to fold the left of the tape towards the middle and adhere firmly. The exemplary micro-fabrication method included a fourth process to attach pre-cut anisotropic conductive film (ACF) lead onto the mid-line of the right square, with the conductive side of the ACF facing up. The exemplary micro-fabrication method included a fifth process to fold the right square towards the middle square and adhere firmly. So far, for example, one single-lead electrode is made. The exemplary micro-fabrication method included a process to repeat the first to fifth processes, e.g., until 3 single-lead electrodes are made. The exemplary micro-fabrication method included a process to peel a piece of Tegaderm open to halfway. The exemplary micro-fabrication method included a process to attach the 3 single-lead electrodes on the adhesive side of the Tegaderm, along the mid-line. The exemplary micro-fabrication method included a process to re-attach (e.g., slowly) the Tegaderm back to its waxy paper. The exemplary micro-fabrication method included a process to solder the 3 ACF leads onto 3 "Deutsches Institut für Normung" (DIN) lead-wire cables.

Figure 8:
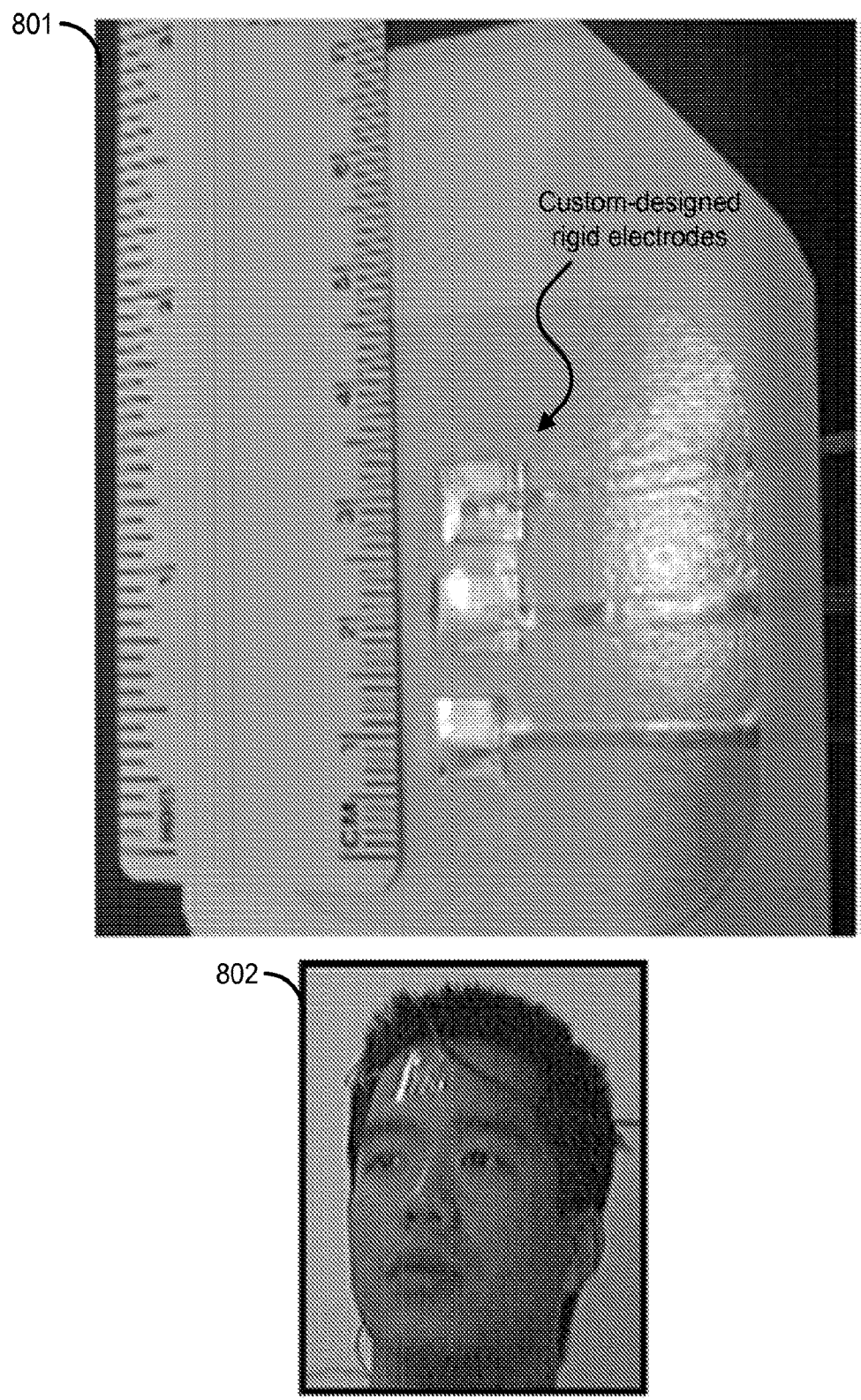
FIG. 8 shows an image of exemplary fabricated, custom-designed rigid electrodes.

The exemplary 3 DIN lead-wire cables served as inputs to the EEG recording system. FIG. 8 shows an image 801 of the exemplary fabricated, custom-designed rigid electrodes. In the image 802 of FIG. 8, the application of this exemplary frontal three-electrode gradient potential (vertical-sagittal) configuration is illustrated on an exemplary subject.

Figure 9A:
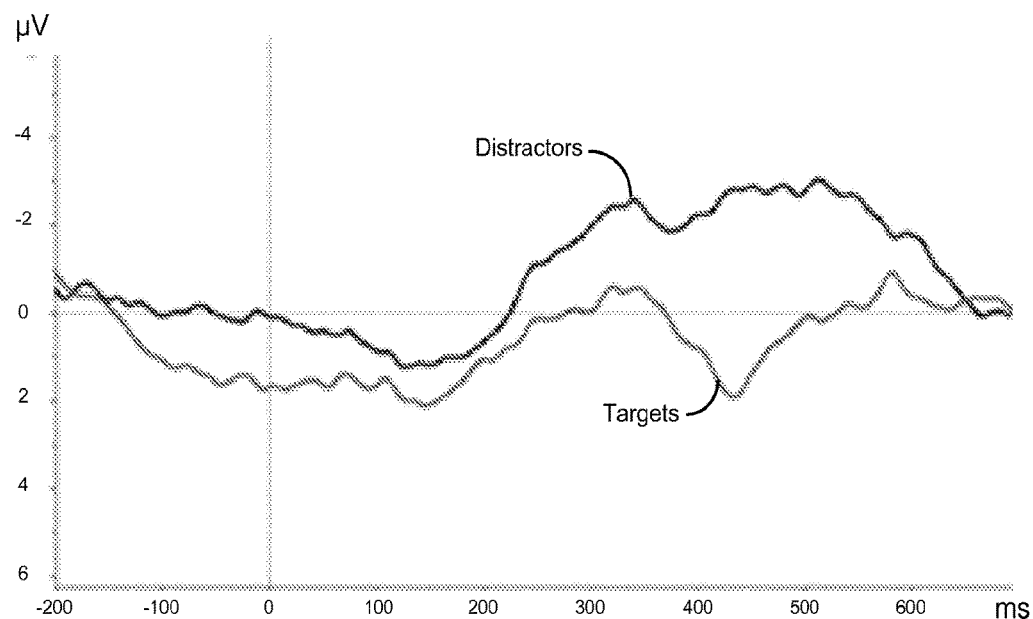
FIGS. 9A-9D show exemplary data plots of ERP waveforms acquired using various exemplary rigid electrodes from a single subject for "Targets", "Distractors", and "Reward".
Figure 9B:
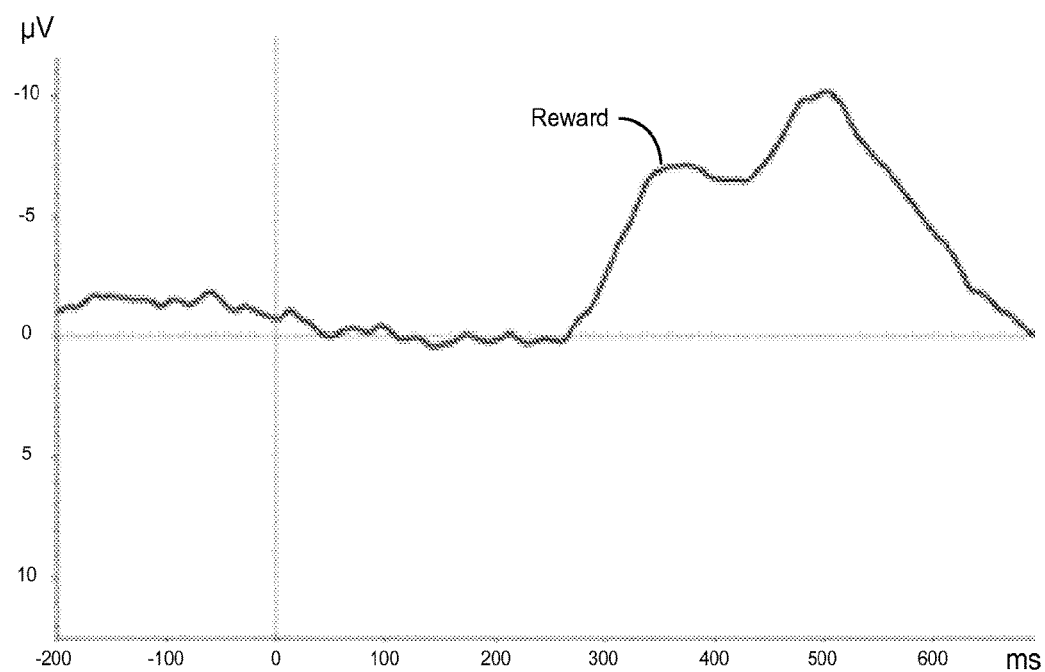
Figure 9C:
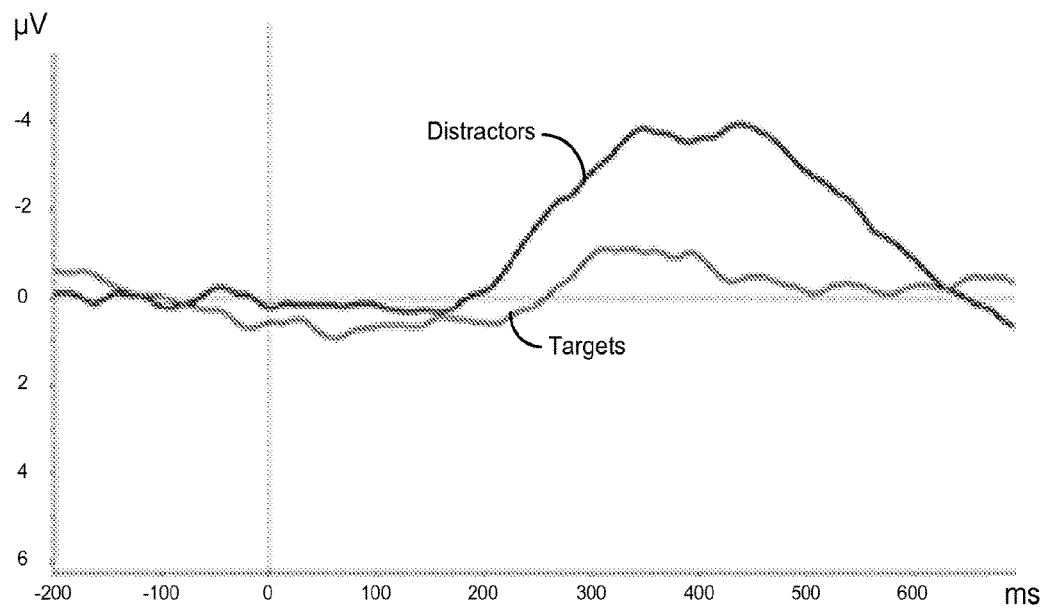
Figure 9D:
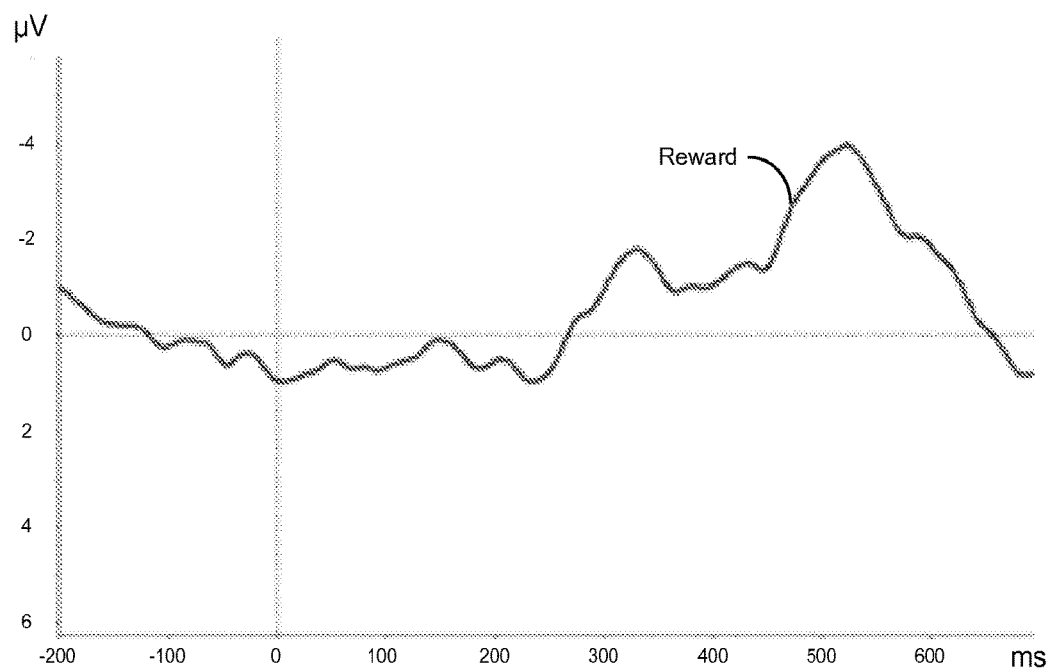

FIG. 9A shows an exemplary data plot of ERP waveforms acquired using the exemplary rigid electrodes (e.g. obtained from Brain Products) from a single subject for "Targets" (red line) and "Distractors" (black line) using the "vertical-sagittal" configuration (gradient potential configuration). FIG. 9B shows an exemplary data plot of ERP waveforms acquired using the exemplary rigid electrodes (e.g. obtained from Brain Products) from a single subject for "Reward" (blue line) using both the "vertical-sagittal" configuration (gradient potential configuration). FIG. 9C shows an exemplary data plot of ERP waveforms acquired using the exemplary custom-designed rigid electrodes from a single subject for "Targets" (red line) and "Distractors" (black line) using the "vertical-sagittal" configuration (gradient potential configuration). FIG. 9D shows an exemplary data plot of ERP waveforms acquired using the exemplary custom-designed rigid electrodes from a single subject for "Reward" (blue line) using both the "vertical-sagittal" configuration (gradient potential configuration). As shown in FIGS. 9A-9D, the exemplary custom-designed sensors can also adequately detect all tested ERPs in the "vertical-sagittal" configuration (gradient potential configuration), e.g., Targets vs. Distractors N=134, F=9.26, p<0.005; and Reward N=43, T=−−2.42, p<0.05. The disclosed three-electrode frontal vertical-sagittal configuration (gradient potential configuration) is capable of efficient ERP detection using various type rigid electrodes.

I.6.3. Using Epidermal Electronics Sensors in Frontal Configurations

Figure 10:
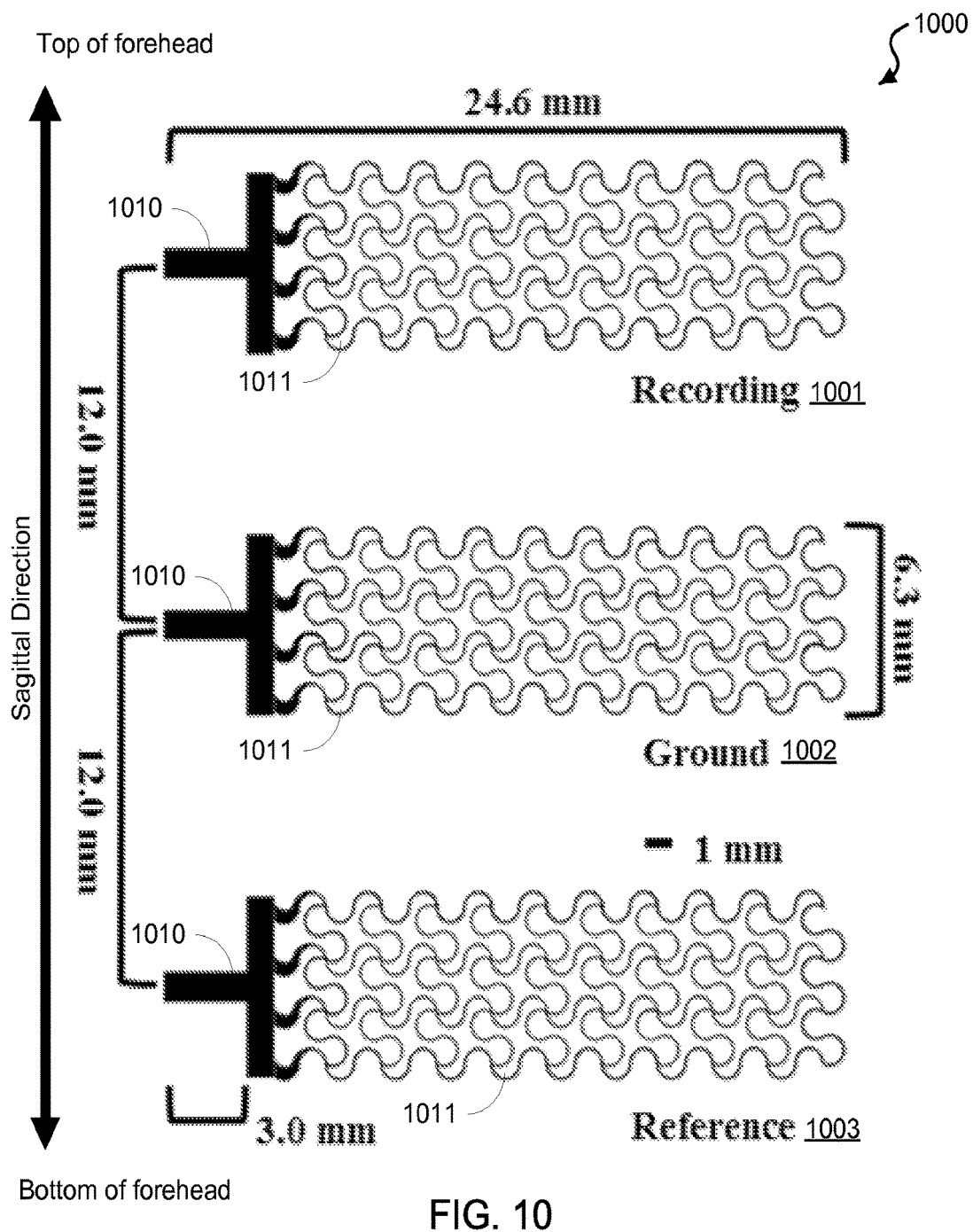
FIG. 10 shows a schematic of an exemplary epidermal electronics frontal three-electrode design.

FIG. 10 shows a schematic of an exemplary EES frontal three-electrode design 1000. The exemplary EES frontal three-electrode design 1000 can be used to configure the electrodes of the device 100, as shown in the diagram of FIG. 1A. As shown in FIG. 10, the EES frontal three-electrode design 1000 includes a recording electrode 1001 structured to include ultrathin electrode islands 1010 with protruding, serpentine-like wires 1011, which all rest on a biologically inert, flexible, stretchable, and/or conforming substrate (e.g., polymer). The EES frontal three-electrode design 1000 includes a ground electrode 1002 separated from the recording electrode 1001 on the substrate by a first distance (e.g., in this example, 12.0 mm) and structured to include the electrode islands 1010 and the protruding, serpentine-like wires 1011. The EES frontal three-electrode design 1000 includes a reference electrode 1003 separated from the ground electrode 1002 on the substrate by a second distance (e.g., in this example, 12.0 mm) and structured to include the electrode islands 1010 and the protruding, serpentine-like wires 1011. The arrangement of the recording electrode 1001, ground electrode 1002, and the reference electrode 1003 are aligned in the sagittal direction. In this example, the electrode island structures 1010 are configured to have two perpendicular ends, where one end is aligned in parallel with the protruding, serpentine-like wires 1011 and having a 3.0 mm size, while the other end is aligned perpendicular with the protruding, serpentine-like wires 1011 and having a 6.3 mm size. Other examples of the exemplary EES frontal three-electrode design 1000 can include different sizes and spacings of the electrode structures.

Figure 11:
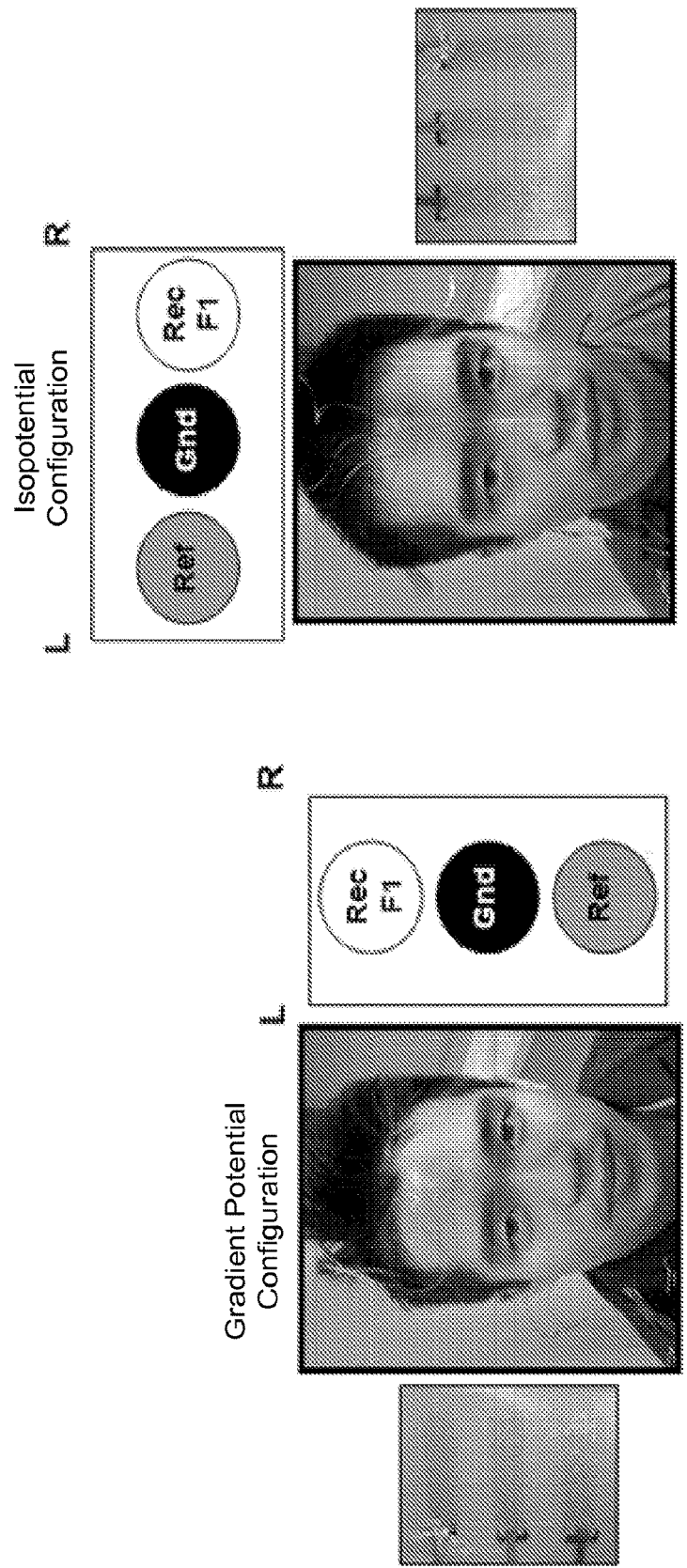
FIGS. 11A and 11B show exemplary three-electrode configurations using exemplary flexible epidermal electrodes along a gradient potential configuration and along an isopotential configuration, respectively.

In this example, the two exemplary frontal configurations, horizontal anatomical alignment of the electrodes along the transverse direction and the vertical anatomical alignment of the electrodes along the sagittal direction, were implemented using the flexible EES sensors. In the vertical-sagittal configuration (gradient potential configuration), the three sensors were placed from the top of the forehead towards the nose, as follows: "Recording F1" electrode, "Ground" electrode, "Reference" electrode, as shown in FIG. 11A. In the horizontal-transverse configuration (isopotential configuration), the three sensors were placed along the forehead from left to right, as follows: "Reference" electrode, "Ground" electrode, "Recording F1" electrode, as shown in FIG. 11B.

Exemplary implementations of the disclosed frontal electrode physiological sensor configurations were performed using an epidermal electronics system. For example, in such implementations, the subject's forehead was first cleaned using an alcohol swab and sterile gauze. After allowing the alcohol to dry, exemplary three-electrode EES flexible sensor devices were placed on the subject's forehead. Each of three sheets of ACF was electrically coupled to a DIN cable on one end and electrically bonded to the EES device's interface pads on the other, aimed toward the subject's right hand side. For example, the subject was instructed to tilt his/her head back as the EES device was wet with tap water using a curved, plastic syringe. At the same time, the subject used a paper towel to cover their eyes from the water. The EES device was gently rubbed until it adhered and was flush with the subject's forehead. In some examples, a no-sting liquid bandage was used to more firmly bond the EES device to the forehead. While allowing the bandage to dry, the EES device's DIN cables were taped to the subject's head using masking tape. For example, this prevented the cables from falling into the subject's field of view and also prevented the cables from pulling on the EES device itself. Also for example, the DIN cables were clipped to the subject's shirt collar to prevent pulling. The DIN cables were subsequently plugged into a traditional EEG amplification system.

Figure 12:
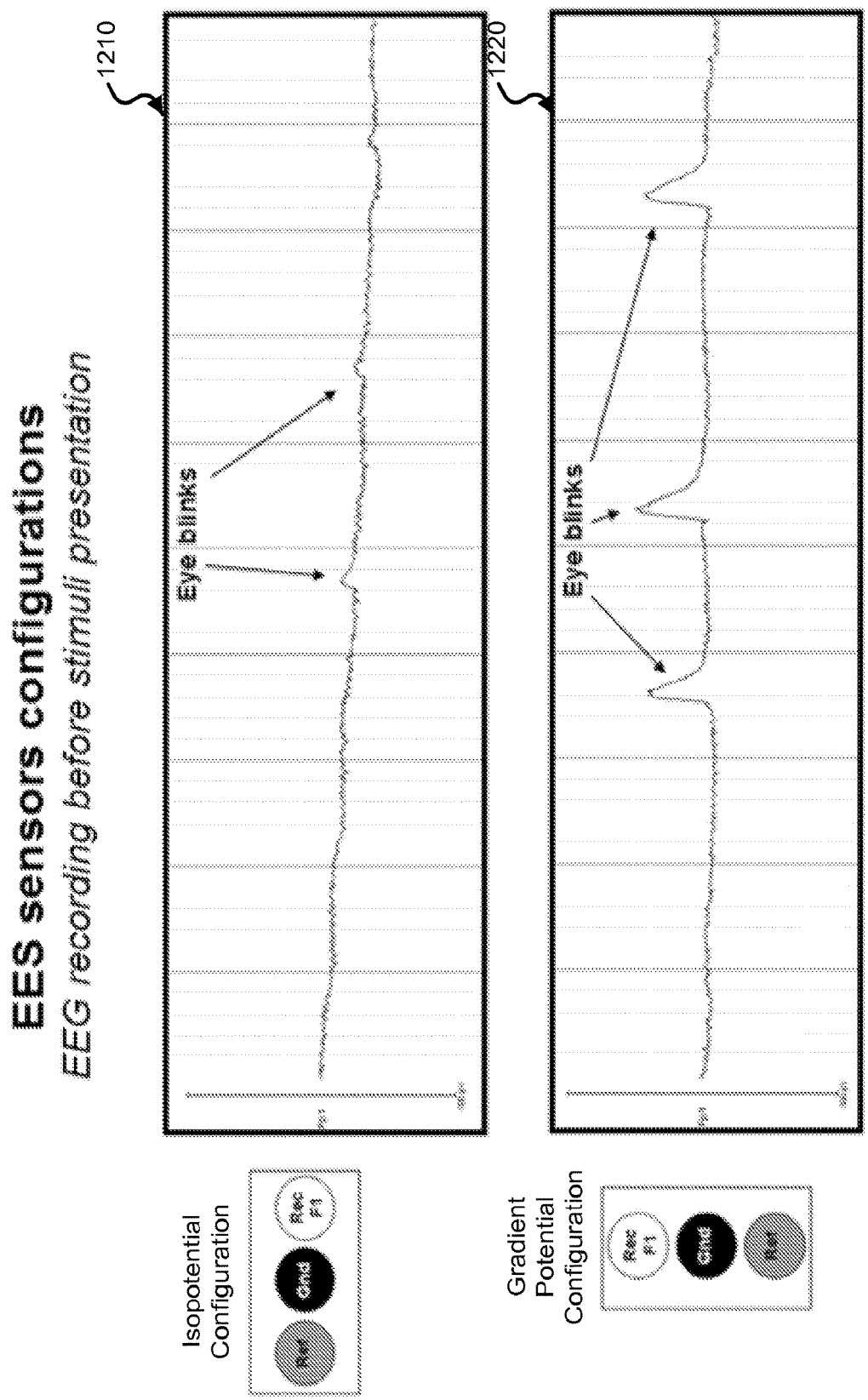
FIG. 12 shows data plots of an exemplary EEG online recording using the exemplary flexible epidermal electrodes before stimuli presentation for both gradient potential and isopotential configurations.

FIG. 12 shows data plots of an exemplary EEG online recording acquired using the exemplary EES flexible electrodes before stimuli presentation for both gradient potential and isopotential configurations. The data plot 1210 shows the exemplary EEG data for the isopotential configuration of the exemplary three-electrode frontal flexible EES sensors. The data plot 1220 shows the exemplary EEG response data for the gradient potential configuration of the exemplary three-electrode frontal flexible EES sensors. Eye blinks were used to better illustrate the signal-to-noise (SNR) ratio of the response in this example.

Figure 13:
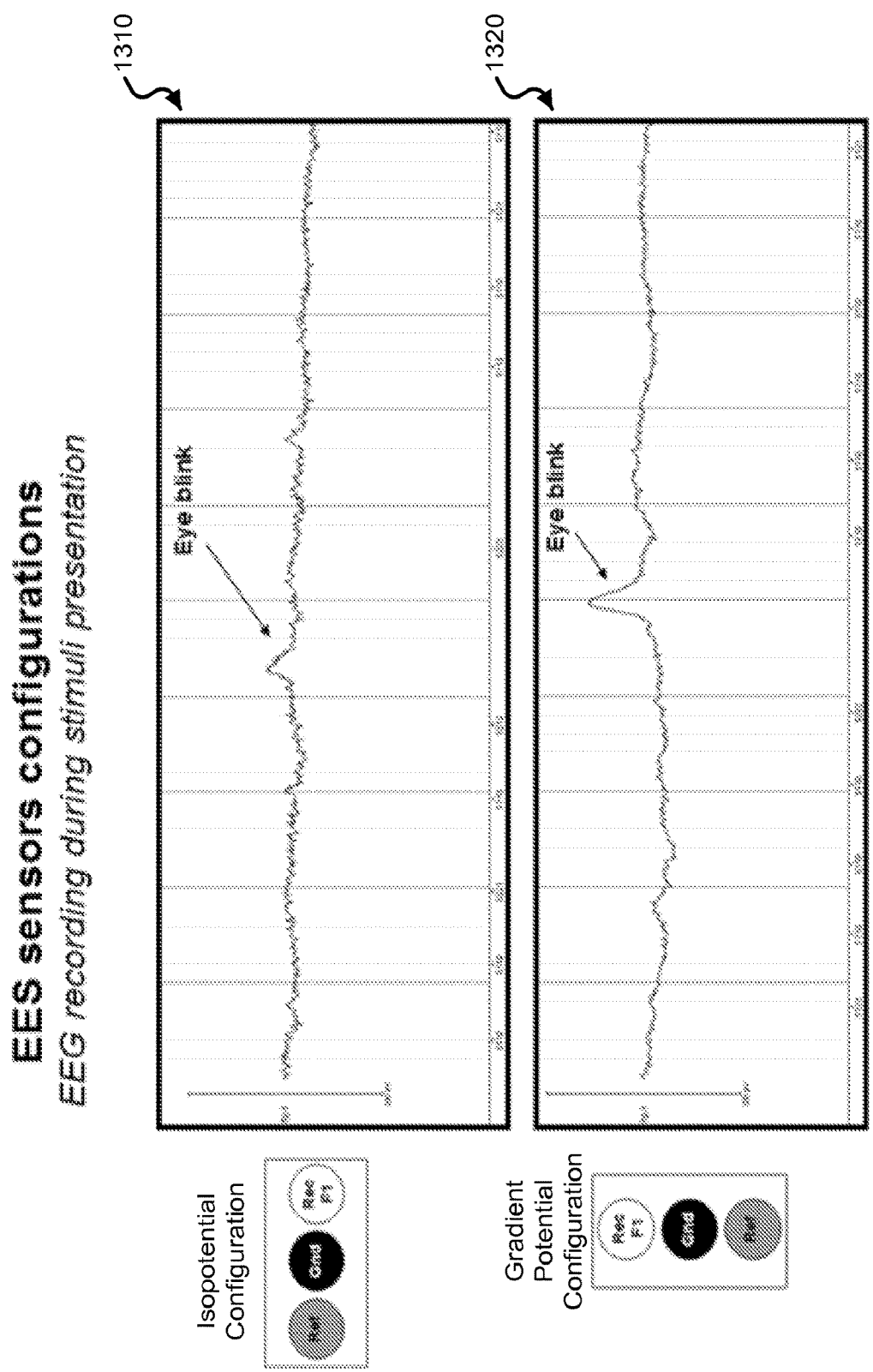
FIG. 13 shows data plots of an exemplary EEG online recording using the exemplary flexible epidermal electrodes during an exemplary stimuli presentation for both gradient potential and isopotential configurations.

FIG. 13 shows data plots of an exemplary EEG online recording acquired using the exemplary EES flexible electrodes during an exemplary stimuli presentation for both gradient potential and isopotential configurations. The data plot 1310 shows the exemplary EEG data for the isopotential configuration of the exemplary three-electrode EES flexible sensors. The data plot 1320 shows the exemplary EEG response data for the gradient potential configuration of the exemplary three-electrode EES flexible sensors. Eye blinks were used to better illustrate the signal-to-noise (SNR) ratio of the response in this example.

As shown in FIGS. 12 and 13, it is noted that in both cases the eye blinks are more pronounced in the gradient potential directions as compared to the isopotential ones, e.g., indicating a better performance, as predicted, for the "vertical-sagittal" configuration.

Figure 14A:
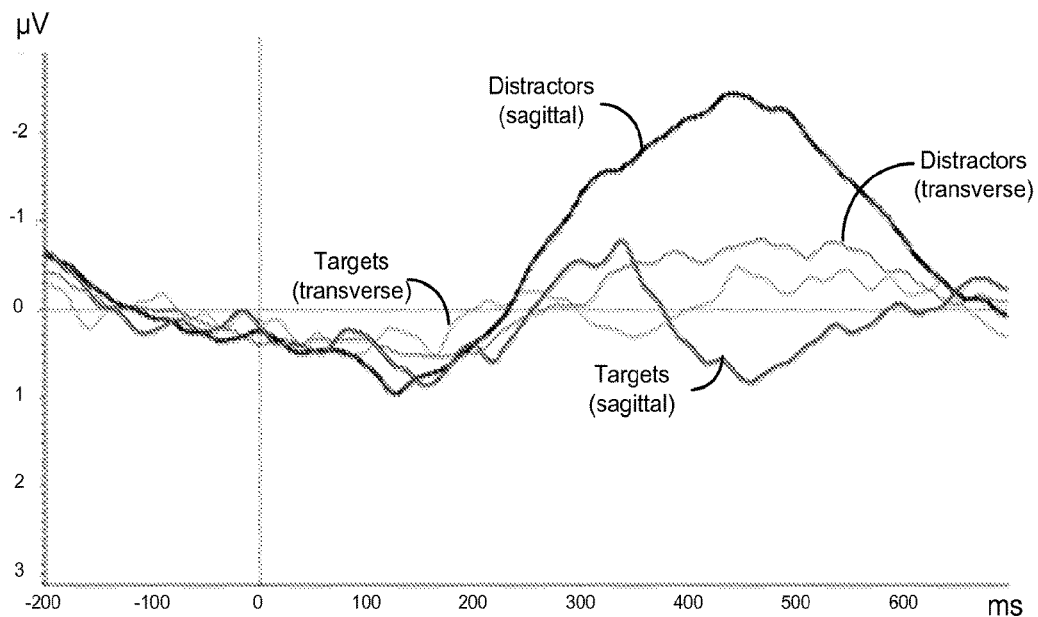
FIG. 14A shows an exemplary data plot of ERP waveforms from a single subject for "Targets" and "Distractors" using the exemplary flexible epidermal electrodes.

FIG. 14A shows an exemplary data plot of ERP waveforms acquired using the exemplary EES flexible electrodes from a single subject for "Targets" (red line) and "Distractors" (black line) using both the "vertical-sagittal" configuration (gradient potential configuration, shown by thicker lines) and the "horizontal-transverse" configuration (isopotential configuration, shown by thinner lines).

Figure 14B:
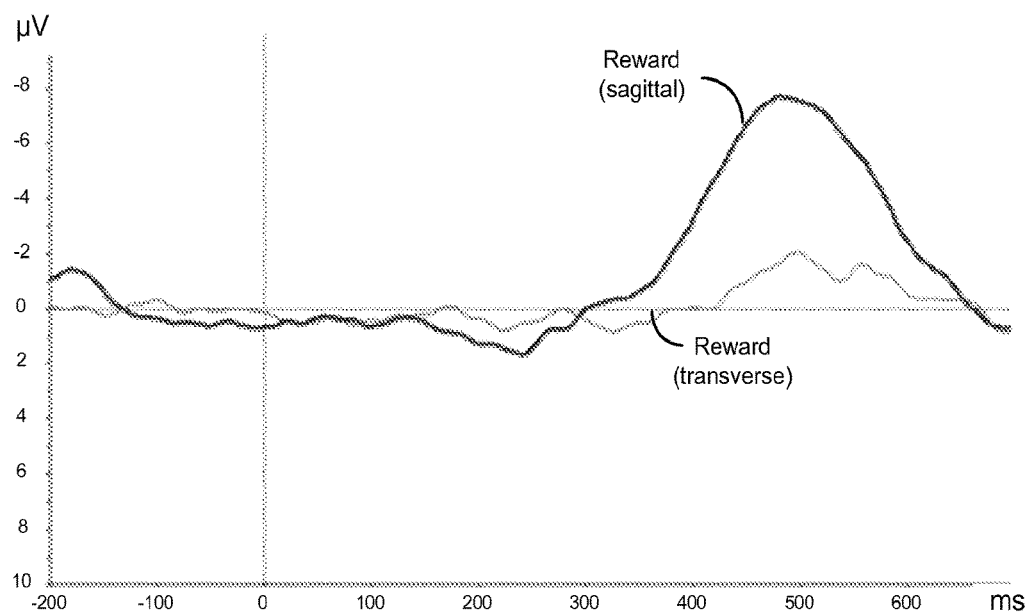
FIG. 14B shows an exemplary data plot of ERP waveforms from a single subject for "Reward" using the exemplary flexible epidermal electrodes.

FIG. 14B shows an exemplary data plot of ERP waveforms acquired using the exemplary EES flexible electrodes from a single subject for "Reward" (blue line) using both the "vertical-sagittal" configuration (gradient potential configuration, shown by thicker lines) and the "horizontal-transverse" configuration (isopotential configuration, shown by thinner lines).

The exemplary results of the exemplary implementations using the exemplary EES flexible electrodes showed adequate detection for all tested ERPs across the isopotential line in the gradient potential configuration, e.g., Targets vs. Distractors N=178, F=12.69, p<0.0005; Reward N=45, T=−3.39, p<0.005. Conversely, the exemplary results of the exemplary implementations using the exemplary EES flexible electrodes showed inadequate detection for all tested ERPs along the isopotential configuration, e.g., Targets vs. Distractors N=178, F=2.39, p=0.12; Reward N=45, T=−1.74, p=0.08. The disclosed three-electrode frontal configuration using the gradient potential configuration is capable of efficient ERP detection using EES flexible electrodes.

II. Mismatch Negativity

Mismatch negativity (MMN) is an ERP modulation that can be correlated with a wide range of neurological and neuropsychiatric disorders. MMN is thought to reflect pre-attentive detection of a deviant stimulus and can be calculated as the difference wave between the responses to deviants (e.g., infrequent) and to standard (e.g., frequent) stimuli in an 'oddball' paradigm. For example, scientific studies on patients suffering from a variety of mental disorders, e.g., including schizophrenia, Alzheimer's disease, and autism spectrum disorder (ASD), have systematically reported that these patient show a decreased ability to detect novel stimuli than healthy subjects. Consistent with this behavior deficit, the amplitude of the MMN is reduced, and thus the MMN can be treated as a marker of either progressive pathology or vulnerability for these disorders.

I.1. Exemplary MMN Implementations

Figure 15:
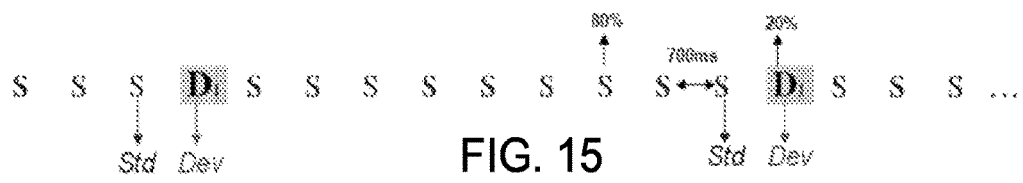
FIG. 15 shows a diagram of an exemplary sequence of stimuli for a mismatch negativity ERP.

Exemplary implementations of the MMN using rigid and flexible EES electrode sensors were performed on subjects. For example, the stimuli were comprised of auditory stimuli using 1500 Hz pure tones of varying intensities (e.g., 50 and 80 dB) with durations of 100 ms (10 ms rise/fall), with 700 ms between tones. FIG. 15 shows a diagram of an exemplary sequence of stimuli for the MMN oddball paradigm. For example, in the diagram of FIG. 15, the 'S' represents a standard stimulus and 'D' represents a deviant stimulus. In the exemplary sequence of stimuli, deviants were used 20%, and standards were used 80%. The exemplary implementations included two conditions, for example: condition 1: standard-low and deviant high; and condition 2: standard-high and deviant low. Each comprised of 1040 trials (e.g., standards and deviants (ratio of deviants to standards was 1:4)).

Figure 16A:
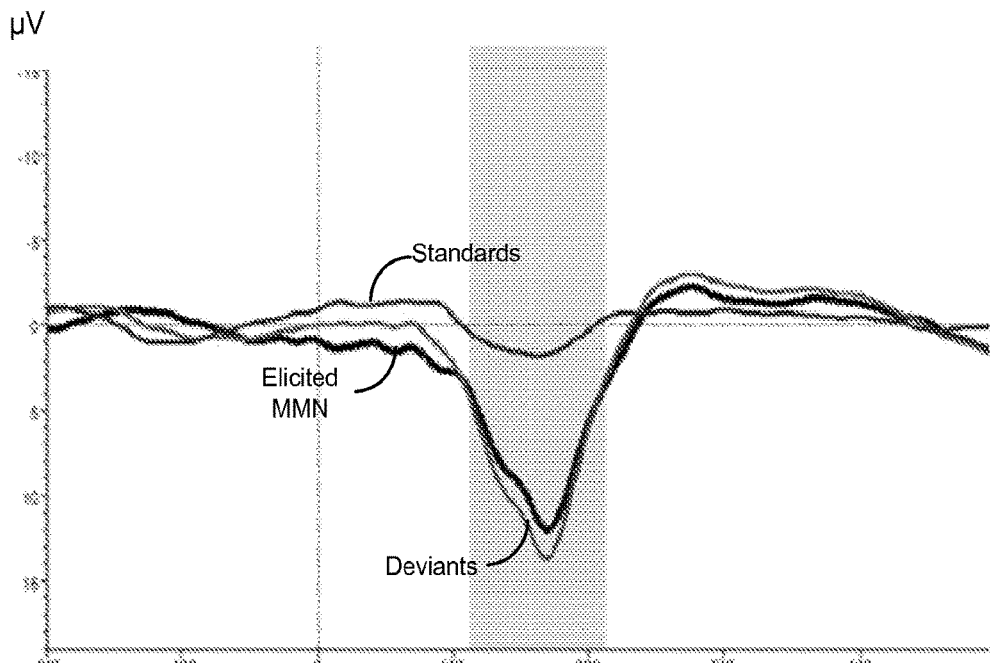
FIGS. 16A and 16B show data plots of exemplary group average ERP waveforms of the elicited mismatch negativity, deviants and standards in a frontal channel of an exemplary rigid EEG electrode cap and with flexible epidermal electrode sensors, respectively.
Figure 16B:
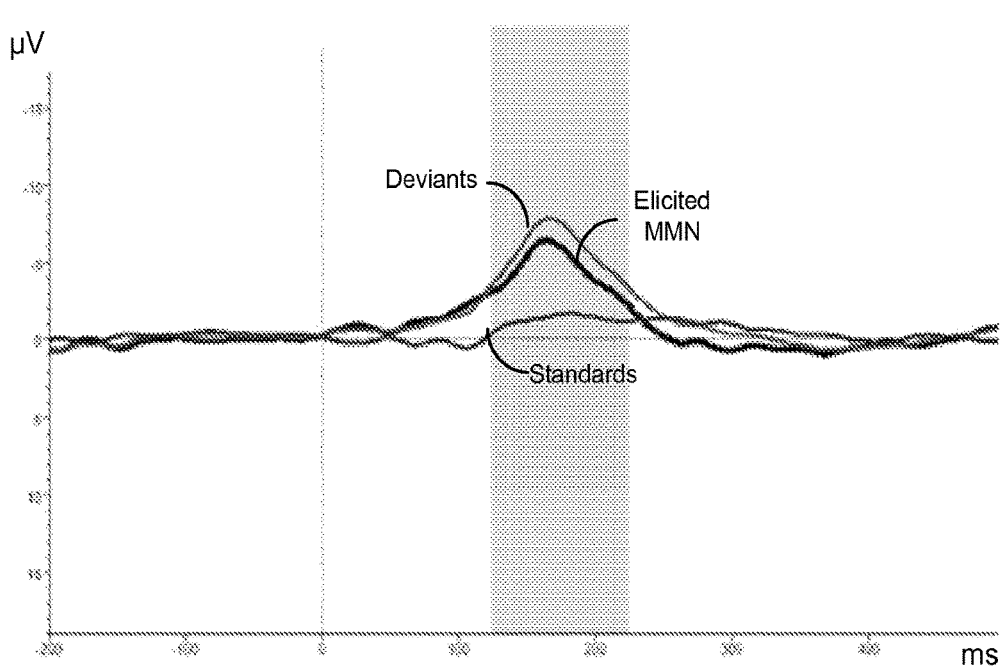

FIG. 16A shows a data plot of exemplary group average (e.g., from 5 subjects) of ERP waveforms of the elicited MMN (black line), deviants (red line) and standards (blue line) in a frontal channel of an exemplary rigid EEG electrode cap, (e.g., N=1017; F=93.976; p<0.001). FIG. 16B shows a data plot of exemplary group average (e.g., from 5 subjects) of ERP waveforms of the elicited MMN (black line), deviants (red line) and standards (blue line) using an exemplary flexible EES 3-electrode sensor with the above-mentioned sagittal (gradient potential) configuration on the subjects' forehead, (e.g., N=1251; F=51.520; p<0.001).

Figure 16C:
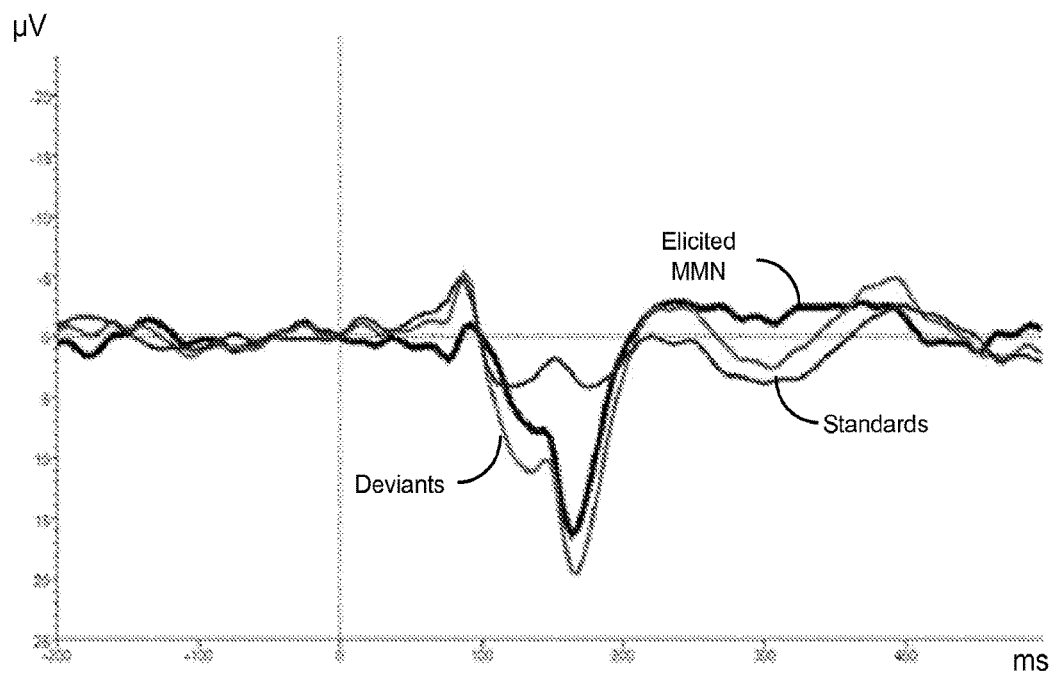
FIGS. 16C and 16D also show data plots of exemplary ERP waveforms a single subject of the elicited mismatch negativity, deviants and standards in a frontal channel of an exemplary rigid EEG electrode cap and with flexible epidermal electrode sensors, respectively.
Figure 16D:
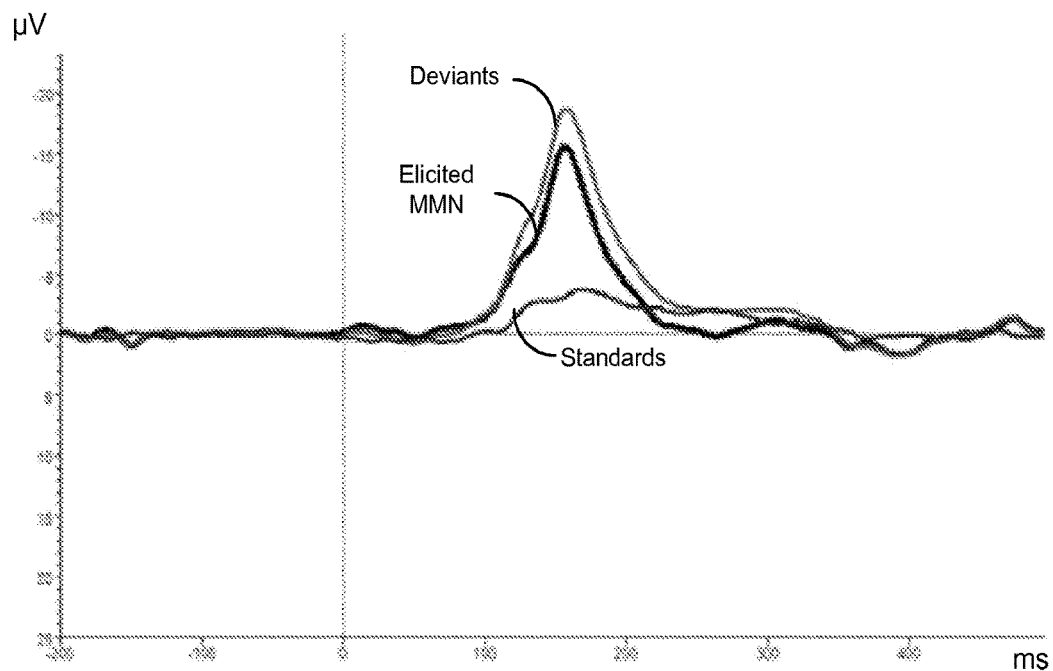

FIG. 16C shows a data plot of exemplary ERP waveforms from a single subject of the elicited MMN (black line), deviants (red line) and standards (blue line) in a frontal channel of an exemplary rigid EEG electrode cap, (e.g., N=128; F=36.567; p<0.001). FIG. 16D shows a data plot of exemplary ERP waveforms from a single subject of the elicited MMN (black line), deviants (red line) and standards (blue line) using an exemplary flexible EES 3-electrode sensor with the abovementioned sagittal (gradient potential) configuration on the subject's forehead (e.g., N=129; F=109.06; p<0.001).

Implementations of the subject matter and the functional operations described in this patent document can be implemented in various systems, digital electronic circuitry, or in computer software, firmware, or hardware, including the structures disclosed in this specification and their structural equivalents, or in combinations of one or more of them. Implementations of the subject matter described in this specification can be implemented as one or more computer program products, i.e., one or more modules of computer program instructions encoded on a tangible and non-transitory computer readable medium for execution by, or to control the operation of, data processing apparatus. The computer readable medium can be a machine-readable storage device, a machine-readable storage substrate, a memory device, a composition of matter effecting a machine-readable propagated signal, or a combination of one or more of them. The term "data processing apparatus" encompasses all apparatus, devices, and machines for processing data, including by way of example a programmable processor, a computer, or multiple processors or computers. The apparatus can include, in addition to hardware, code that creates an execution environment for the computer program in question, e.g., code that constitutes processor firmware, a protocol stack, a database management system, an operating system, or a combination of one or more of them.

A computer program (also known as a program, software, software application, script, or code) can be written in any form of programming language, including compiled or interpreted languages, and it can be deployed in any form, including as a stand-alone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application specific integrated circuit).

Processors suitable for the execution of a computer program include, by way of example, both general and special purpose microprocessors, and any one or more processors of any kind of digital computer. Generally, a processor will receive instructions and data from a read only memory or a random access memory or both. The essential elements of a computer are a processor for performing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Computer readable media suitable for storing computer program instructions and data include all forms of nonvolatile memory, media and memory devices, including by way of example semiconductor memory devices, e.g., EPROM, EEPROM, and flash memory devices. The processor and the memory can be supplemented by, or incorporated in, special purpose logic circuitry.

While this patent document contains many specifics, these should not be construed as limitations on the scope of any invention or of what may be claimed, but rather as descriptions of features that may be specific to particular embodiments of particular inventions. Certain features that are described in this patent document in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. Moreover, the separation of various system components in the embodiments described in this patent document should not be understood as requiring such separation in all embodiments.

Only a few implementations and examples are described and other implementations, enhancements and variations can be made based on what is described and illustrated in this patent document.

What is claimed is:

1. An electroencephalography (EEG) system, comprising:
    an EEG sensor device comprising a substrate formed of an electrically insulative material and structured to allow physical contact of the device with a forehead of a user;
    a first electrode configured at a first location on the substrate to acquire an EEG signal of the user from the user's forehead;
    a second electrode configured at a second location on the substrate to acquire a second EEG signal of the user as a reference signal to the EEG signal; and
    a third electrode configured on the substrate to acquire a third EEG signal of the user as an electrical ground signal,
    wherein the third electrode is configured at a third location at least partially between the first and the second locations on the substrate, and the first location is configured above the second and third locations along a vertical direction in a frontal plane when the EEG sensor device is placed on the forehead of the user, and wherein the first electrode and the second electrode are spaced apart by at most 24 mm, and
    wherein, when electrically coupled to an electrical circuit, the device is operable to detect physiological signals of the user,
    wherein the device is implemented in the system to provide a cognitive or sensory assessment, wherein the system further comprises a data processing system in communication with the EEG sensor device and includes one or more memory units and one or more processors configured to process the detected physiological signals as physiological data to generate an information set including one or more quantitative values associated with a cognitive-sensory profile category indicative of one or more aspects of cognitive or sensory functions.

2. The system as in claim 1, wherein the first, second, and third electrodes are linearly arranged on the substrate.

3. The system as in claim 1, wherein the substrate is formed of a mechanically flexible material structured to adhere to skin or a wearable item of the user.

4. The system as in claim 3, further comprising:
    electrical interface components formed separately on the substrate and electrically coupled to the first, second, and third electrodes, respectively, via electrically conductive conduits,
    wherein, when the device is electrically coupled to the electrical circuit, the electrical interface components are electrically coupled to the electrical circuit via wires.

5. The system as in claim 3, further comprising:
    the electrical circuit,
    wherein the electrical circuit includes:
        a signal processing circuit formed on the substrate in electrical communication with the first, second, and third electrodes via electrically conductive conduits, the signal processing circuit to amplify acquired EEG signals, and
        a transmitter unit on the substrate in electrical communication with the signal processing circuit to transmit the amplified EEG signals to the data processing system.

6. The system as in claim 5, further comprising:
    a power supply module electrically coupled to the electrical circuit to provide electrical power to the transmitter unit.

7. The system as in claim 5, wherein the EEG sensor device is configured as a wearable patch worn on the user's scalp.

8. The system as in claim 5, wherein the EEG sensor device is configured in a region of a wearable item capable of physical contact with the user's scalp.

9. The system as in claim 1, further comprising:
    a fourth electrode configured at a fourth location on the substrate to acquire a fourth EEG signal of the user; and
    a fifth electrode configured at a fifth location on the substrate to acquire a fifth EEG signal of the user,
    wherein the fourth location is configured left of the first location, and the fifth location is configured right of the first location.

10. The system as in claim 1, wherein the one or more processors of the data processing system are configured to process the physiological signals detected by the EEG sensor device to generate the information set by:
    selecting time intervals of interest within the physiological data based on the presented stimuli and the cognitive-sensory profile category,
    grouping, into one or more grouped data sets, the physiological data corresponding to the selected time intervals of interest, and
    providing a statistical measure of a relationship across or within the grouped data sets to generate the one or more quantitative values.

11. The system as in claim 1, wherein the one or more quantitative values includes a quantitative score depicting a level of one or both of cognitive and sensory performance based on at least one of the user's attention, memory, learning ability, confabulation characteristics, pattern integration ability, semantic integration ability, target detection ability, emotional valence, preference, or awareness, and wherein the quantitative score depicts the level at a particular time.

12. The system as in claim 1, wherein the system further comprises:
    a stimulus delivery device to produce a sequence of stimuli based on the cognitive-sensory profile category that is presented to the user wearing the EEG sensor device, wherein the stimuli includes at least one of a visual, auditory, olfactory, tactile, or gustatory stimulating medium,
wherein the EEG sensor device is interfaced to the user to detect the physiological signals exhibited by the user before, during, and after a presentation of the sequence of stimuli.

13. The system as in claim 1, wherein the data processing system includes:
a local computer proximate to and in communication with the EEG sensor device to receive the detected physiological signals from the EEG sensor device, the local computer configured to conduct initial processing of the detected physiological signals to produce initial physiological signal data, and
a remote computer in communication with the local computer via a communication network or link to receive the initial physiological signal data from the local computer and to process the initial physiological signal data to generate the information set including one or more quantitative values associated with the cognitive-sensory profile category.

14. The system as in claim 13, wherein the local computer is a mobile communications device including a smartphone or tablet that is in wireless communications with the EEG sensor device.

15. A wearable physiological sensor device, consisting of:
a substrate formed of a mechanically flexible and an electrically insulative material and structured to allow physical contact of the device with a forehead of a user;
three electrodes on the substrate arranged along a vertical direction in a frontal plane when the physiological sensor device is placed on the forehead of the user, including:
a first electrode configured at a first location on the substrate to acquire an electrophysiological signal of the user,
a second electrode configured at a second location below the first location on the substrate to acquire a second electrophysiological signal of the user as a reference signal to the electrophysiological signal,
a third electrode configured at a third location at least partially between the first and the second locations on the substrate to acquire a third electrophysiological signal of the user as an electrical ground signal,
wherein the first electrode and the second electrode are spaced apart by at most 24 mm;
an electrical circuit on the substrate in electrical communication with the first, second, and third electrodes via electrically conductive conduits, the electrical circuit including an amplification circuit and a signal processing circuit to amplify and signal process the electrophysiological signals;
a transmitter unit on the substrate in electrical communication with the electrical circuit to transmit the amplified and signal processed electrophysiological signals to at least one of a data processing unit or a remote computer system; and
a power supply module electrically coupled to the transmitter unit to provide electrical power to the transmitter unit.

16. The device as in claim 15, wherein the first, second, and third electrodes are linearly arranged on the substrate.

17. The device as in claim 15, wherein the mechanically flexible substrate is structured to adhere to skin or a wearable item of the user.

18. An electroencephalography (EEG) sensor device, comprising:
a substrate formed of an electrically insulative material and structured to allow physical contact of the device with a forehead of a user;
a first electrode configured at a first location on the substrate to acquire an EEG signal of the user from the user's forehead;
a second electrode configured at a second location on the substrate to acquire a second EEG signal of the user as a reference signal to the EEG signal;
a third electrode configured on the substrate to acquire a third EEG signal of the user as an electrical ground signal,
wherein the third electrode is configured at a third location at least partially between the first and the second locations on the substrate, and the first location is configured above the second and third locations along a vertical direction in a frontal plane when the EEG sensor device is placed on the forehead of the user, and wherein the first electrode and the second electrode are spaced apart by at most 24 mm; and
an electrical circuit including a signal processing circuit formed on the substrate in electrical communication with the first, second, and third electrodes via electrically conductive conduits, the signal processing circuit to amplify acquired EEG signals, and a transmitter unit on the substrate in electrical communication with the signal processing circuit to transmit the amplified EEG signals to at least one of a data processing unit or a remote computer system,
wherein the device is operable to detect physiological signals of the user.

19. The device as in claim 18, wherein the substrate is formed of a mechanically flexible material structured to adhere to skin or a wearable item of the user.

20. The device as in claim 18, further comprising:
a fourth electrode configured at a fourth location on the substrate to acquire a fourth EEG signal of the user; and
a fifth electrode configured at a fifth location on the substrate to acquire a fifth EEG signal of the user,
wherein the fourth location is configured left of the first location, and the fifth location is configured right of the first location.

21. A method to provide a cognitive or sensory assessment of a subject, comprising:
acquiring EEG signals of the subject from the frontal region of the subject's head to produce physiological data using a system comprising a sensor device including:
a substrate formed of an electrically insulative material and structured to allow physical contact of the sensor device with the frontal region of the head of the subject, and
three electrodes including a recording electrode, a reference electrode, and a ground electrode to acquire the EEG signals of the subject from three respective positions arranged on the substrate along a vertical direction of the frontal region, wherein the recording electrode is configured above the ground and reference electrodes, and the ground electrode is configured between the recording and reference electrodes, and wherein the recording electrode and the reference electrode are spaced apart by at most 24 mm, and wherein the sensor device is implemented in the system to provide a cognitive or sensory assessment, wherein the system further comprise a data processing system in communication with the sensor device and includes one or more memory units and one or more processors configured to process the acquired EEG signals as physiological data; and processing, by the system, the physiological data to generate an information set including one or more quantitative values associated with a cognitive-sensory profile category indicative of one or more aspects of cognitive or sensory functions.

22. The method as in claim 21, further comprising:

presenting a sequence of stimuli to the subject, the sequence of stimuli based on the cognitive-sensory profile category, wherein the acquiring the EEG signals is implemented before, during, and after the presenting the sequence of stimuli.

23. The method as in claim 22, further comprising:

selecting the cognitive-sensory profile category from among a cognitive performance profile, a sensory performance profile, and a cognitive and sensory performance profile.

24. The method as in claim 22, wherein the sequence of stimuli includes at least one of a visual, auditory, olfactory, tactile, or gustatory stimulating medium based on the selected cognitive-sensory profile category.

25. The method as in claim 21, wherein the one or more quantitative values include a quantitative score depicting a level of one or both of cognitive and sensory performance based on at least one of the subject's attention, memory, learning ability, confabulation characteristics, pattern integration ability, semantic integration ability, target detection ability, emotional valence, preference, or awareness state, and wherein the quantitative score depicts the level at a particular time.

26. The method as in claim 21, wherein the processing includes:

identifying a time interval associated with the EEG signals based on the cognitive-sensory profile category, grouping the physiological data corresponding to the time interval into one or more grouped data sets, and providing a statistical measure of a relationship across or within the grouped data sets to generate the one or more quantitative values for the selected cognitive-sensory profile category.

* * * * *